(12) United States Patent
Wilson et al.

(10) Patent No.: US 8,799,011 B2
(45) Date of Patent: *Aug. 5, 2014

(54) PATIENT ROOM AND BED MANAGEMENT APPARATUS AND SYSTEM

(75) Inventors: Bradley T. Wilson, Batesville, IN (US); Whitney W. Pesot, Cary, NC (US); Katherine J. Vigneron, Blaine, MN (US); Michelle E. McCleerey, Raleigh, NC (US); Christian Saucier, Raleigh, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 282 days.

This patent is subject to a terminal disclaimer.

(21) Appl. No.: 12/711,912

(22) Filed: Feb. 24, 2010

(65) Prior Publication Data
US 2011/0208541 A1 Aug. 25, 2011

Related U.S. Application Data

(63) Continuation-in-part of application No. 12/708,891, filed on Feb. 19, 2010, now Pat. No. 8,334,777.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ........................................................... 705/2
See application file for complete search history.

(56) References Cited

U.S. PATENT DOCUMENTS

| | | |
|---|---|---|
| 5,561,412 A | 10/1996 | Novak et al. |
| 5,699,038 A | 12/1997 | Ulrich et al. |
| 5,838,223 A | 11/1998 | Gallant et al. |

(Continued)

OTHER PUBLICATIONS

LeBellego, A model for the measurement of patient activity in a hospital suite,2006, Information Technology in Biomedicine, IEEE Transactions on , vol. 10, No. 1, pp. 92-99.*

*Primary Examiner* — Tran Nguyen
(74) *Attorney, Agent, or Firm* — Barnes & Thornburg LLP

(57) ABSTRACT

A patient room and bed management apparatus and system detects changes in a patient's status and updates the status of a room of a healthcare facility associated with the patient. The system may receive the patient status information from a remote system, such as a health information system used by a healthcare facility. The patient room and bed management system may determine one or more actions to be performed by a bed in the patient's room. The system may determine one or more actions to be performed by a caregiver or other staff person of the healthcare facility. The actions to be performed by the bed or staff person may be triggered by a change in status of the patient, the patient's bed, or the patient's room. The actions to be performed may be electronically communicated to the bed, to one or more remote displays, and/or to communication devices associated with staff persons of the healthcare facility.

The patient room and bed management apparatus and system may include a user interface module that is not mounted to the patient's bed. A list of actions to be performed by a staff person in the patient's room, the status of the patient, the status of the patient's room, and/or the status of the patient's bed, may be displayed and updated electronically at the user interface module. The user interface module may also provide bed controls that allow a staff person to initiate an electronically-controlled function of the bed from the user interface module.

14 Claims, 21 Drawing Sheets

(56) References Cited

U.S. PATENT DOCUMENTS

| | | |
|---|---|---|
| 6,147,592 A | 11/2000 | Ulrich et al. |
| 6,279,183 B1 | 8/2001 | Kummer et al. |
| 6,344,794 B1 | 2/2002 | Ulrich et al. |
| 6,362,725 B1 | 3/2002 | Ulrich et al. |
| 6,897,780 B2 | 5/2005 | Ulrich et al. |
| 6,957,461 B2 | 10/2005 | Osborne et al. |
| 7,092,376 B2 | 8/2006 | Schuman |
| 7,154,397 B2 | 12/2006 | Zerhusen et al. |
| 7,237,287 B2 | 7/2007 | Weismiller et al. |
| 7,242,308 B2 | 7/2007 | Ulrich et al. |
| 7,319,386 B2 | 1/2008 | Collins, Jr. et al. |
| 7,451,506 B2 | 11/2008 | Kummer et al. |
| 7,480,951 B2 | 1/2009 | Weismiller et al. |
| 8,334,777 B2 * | 12/2012 | Wilson et al. ............. 340/573.1 |
| 2003/0074222 A1 * | 4/2003 | Rosow et al. ..................... 705/2 |
| 2006/0058587 A1 | 3/2006 | Heimbrock et al. |
| 2007/0169268 A1 * | 7/2007 | Lemire et al. ..................... 5/617 |
| 2007/0180616 A1 | 8/2007 | Newkirk et al. |
| 2007/0210917 A1 | 9/2007 | Collins, Jr. et al. |
| 2008/0224861 A1 | 9/2008 | McNeely et al. |
| 2008/0235872 A1 | 10/2008 | Newkirk et al. |
| 2009/0212956 A1 | 8/2009 | Schuman et al. |

\* cited by examiner

ROOM READY

[ ZERO SCALE ]

| ROOM | READY | SCALE LAST ZEROED | PATIENT |
|------|-------|-------------------|---------|
| 101-A | ✓ | 01/13 AT 10:30 am | ADMIT: 01/10 AT 8:33 am<br>DISCHARGE: |
| 101-B | ✗ | 01/13 AT 2:48 pm | ADMIT: 01/04 AT 11:27 pm<br>DISCHARGE: 01/13 AT 4:55 pm |

FIG. 10

PATIENT ROOM AND BED MANAGEMENT APPARATUS AND SYSTEM

RELATED APPLICATIONS

This application is a continuation-in-part of and claims priority to U.S. patent application Ser. No. 12/708,891, filed Feb. 19, 2010, which is incorporated herein by this reference in its entirety.

TECHNICAL FIELD

This disclosure relates generally to patient beds, healthcare information systems, and communication systems for hospitals and other healthcare facilities that are equipped with patient beds. More particularly, this disclosure relates to computerized systems in which beds located in patient rooms can be connected to a healthcare facility's computerized information and communication systems.

BACKGROUND

Many hospitals and other healthcare facilities use computerized information systems and communication systems to help manage various aspects of the provision of services to patients. Such facilities often utilize a computerized health information system (HIS) that has admission, discharge, and transfer data collection and communication capabilities. The HIS typically tracks the status of patients during their stay at the facility. The HIS may also maintain an electronic medical records (EMR) database, which typically stores information collected about patients, such as patient demographics, vital signs and test results, during their stay at the facility.

Many healthcare facilities also have an electronic communication system, such as a "nurse call" system, which enables telephonic and/or electronic communication among caregivers or other staff members of the facility and/or between staff members and patients in the facility. Many nurse call systems have a centralized computer system (e.g. a "master station") that monitors and controls the routing of electronic communications to and from patients and caregivers, and a number of remote computer devices (e.g. "patient stations") located in the patient rooms. The patient stations communicate electronically with the master station.

For example, a patient may issue a call to a caregiver by pressing a button located on the patient's bed or on a nearby unit. The call may be answered by a caregiver at the master station. The master station may route the call or a notification thereof to one of the patient stations or to a specific caregiver's phone or other mobile communication device. Some examples of nurse call systems are disclosed in U.S. Patent Application Publication No. 2009/0212956, and U.S. Pat. Nos. 7,242,308; 7,092,376; 6,897,780; 6,362,725; 6,147,592; 5,838,223; 5,699,038; and 5,561,412.

Some hospital systems may have point of care interfaces located in patient rooms of a healthcare facility, which may be connected to a central computer system or server (such as a nurse call system) by a communication network. The point of care interface may take the form of a wall-mounted display that displays information about a patient or equipment in the room. In some systems, the point of care interface includes a user interface, which allows an authorized caregiver or other user to input data to the system, but not to control bed functions, via the point of care interface. For example, some point of care interfaces allow cleaning staff to activate a feature of the interface to indicate that a particular room has been cleaned. Some examples of point of care interfaces are disclosed in U.S. Pat. No. 7,154,397. Some examples of hospital systems that allow an authorized user to indicate whether a patient's room is clean or dirty at a user interface located on a hospital bed or elsewhere in the patient's room, are described in U.S. Pat. Nos. 7,319,386 and 7,154,397.

In some healthcare facilities, caregivers are provided with badges that communicate wirelessly with a locating and tracking system or a locating and tracking feature of a nurse call system or other hospital computer system. Information received from the badges and from receivers located throughout the facility may be used to determine the caregiver's location in the facility. One example of a locating and tracking system is disclosed in U.S. Pat. No. 6,344,794.

Some healthcare facilities use locating and tracking technology to detect whether a caregiver or other staff member is in a particular location, and then cause certain events to occur when the person is at that location. For example, U.S. Pat. No. 7,154,397 discloses a system in which a cleaning status of a room may be updated automatically if a staff member has been in the room for a specified period of time. As another example, U.S. Pat. No. 7,319,386 discloses enabling or disabling functions of a bed when a locating and tracking system detects that a particular caregiver has entered the room in which the bed is located.

Some healthcare facilities are equipped with patient beds that have a number of computerized features and/or features that are electronically controlled. For example, some patient beds are equipped with a weigh scale and an electronic bed control module, so that a caregiver can weigh the patient while the patient is on the bed, simply by touching a button on the bed control module. Some examples of patient beds that have a number of electronically-controlled features are disclosed in U.S. Pat. Nos. 6,957,461 and 6,279,183.

Sometimes, patient beds that have electronically-controlled functions are equipped with an internal bed communication network. For example, one or more bed controllers and bed function modules may be connected to the bed network, so that control signals from the bed controller(s) are communicated to the appropriate bed function modules via the bed network. Some examples of patient beds that have an internal bed network are described in U.S. Pat. Nos. 7,480,951; 7,451,506; and 7,237,287.

Patient beds that have electronically-controlled functions often have one or more bed control modules, which provide a user interface that allows a patient or caregiver to control certain features of the bed. Typically, such bed control modules are mounted to a siderail, endboard, or other support structure of the patient bed. Some examples of bed control modules with user interfaces are disclosed in U.S. Patent Application Publication No. 2007/0180616.

Bed control modules may be connected to the bed through a wired or a wireless connection. One example of a wireless bed controller is disclosed in U.S. Patent Application Publication No. 2006/0058587.

Some bed control modules have a graphical user interface (GUI). On some bed control modules, the graphical user interface may include touch-sensitive input devices. Some examples of bed control modules that have a graphical touch-screen user interface are disclosed in U.S. Patent Application Publication Nos. 2007/0180616 and 2008/0235872.

Some patient beds can be connected to a healthcare facility's nurse call system to send data generated at the bed to the nurse call system. For example, a patient bed may have sensors that detect when a patient has exited a bed, if the bed's brake is not set, or when a siderail is down. Upon detecting such a condition, the bed may send an alert signal to a master station of the facility's nurse call system. The master station may then send an electronic notification to a remote device, such as a patient station or a mobile unit used by a caregiver. Some examples of systems in which beds may communicate data to a hospital communication system are disclosed in U.S. Pat. Nos. 7,319,386; 6,362,725; and 5,699,038.

Patient beds may be connected to a facility's nurse call system via a wired or a wireless connection. Some examples of beds that have wireless data connectivity to hospital nurse call systems are disclosed in U.S. Pat. No. 7,319,386 and U.S. Patent Application Publication Nos. 2008/0224861 and 2007/0210917.

SUMMARY

The present invention comprises one or more of the features recited in the appended claims and/or the following features which, alone or in any combination, may comprise patentable subject matter.

According to one aspect of this disclosure, a bed system includes a bed having a number of electronically-controllable functions and a bed identifier, and a bed control system connected to the bed and configured to control one or more of the electronically-controllable functions of the bed. The bed controller includes memory in which data and computer-executable instructions are stored, a communications interface configured to couple the bed system to a health information system of a healthcare facility, and processor circuitry configured to execute the computer-executable instructions to: receive via the communications interface a patient status signal representative of patient status information from the health information system, the patient status information indicating a status of a patient in the healthcare facility, and send a control signal to the bed to cause the bed to automatically without user intervention initiate one of the electronically-controlled functions of the bed in response to the patient status signal.

The patient status signal may include an admission, discharge and transfer (ADT) indicator. The patient status signal may indicate that the patient has been discharged from the healthcare facility. The bed may have a built-in weigh scale, and the control signal may initiate zeroing of the weigh scale.

According to another aspect of this disclosure, a healthcare communication system includes memory in which data and computer-executable instructions are stored, a communications interface, and processor circuitry configured to execute the computer-executable instructions to: receive via the communications interface a patient status signal representative of patient status information generated at a health information system of a healthcare facility, the patient status signal indicating a status of a patient in the healthcare facility, determine, based on the patient status signal, a status of a room in the healthcare facility, the room having therein a bed associated with the patient, send via the communications interface a room status signal indicating the status of the room to a user interface device located in the patient room to cause the user interface device to indicate the status of the room, generate a list of actions to be performed by a person associated with the healthcare facility in the room associated with the patient, the list of actions being generated in accordance with the room status, the person being someone other than the patient, the list of actions including at least one bed-related activity and at least one room-related activity, and send via the communications interface the list of actions to an input/output device.

The status of the patient may be one of admitted, transferred, or discharged. The status of the room may be one of clean, needs cleaning, and ready for new patient.

The bed-related activity or activities may relate to at least one of: raising the bed siderails, setting a bed brake, placing the bed in a low position, arming or disarming a bed patient position monitoring (PPM) system, arming or disarming a head of bed angle monitoring system, placing sheets on the bed, and zeroing a weigh scale of the bed.

The room-related activity or activities may relate to at least one of clean the room, remove obstructions to room exit, prepare bed for new patient, indicate whether room preparations are complete, and indicate whether a caregiver's round is complete.

The list of actions may include at least one patient-related activity. The one or more patient-related action(s) may include at least one of taking patient's temperature, giving patient a pillow, and giving patient a garment.

The processor circuitry may be configured to execute computer-executable instructions to receive user input at the user interface device, and the user input relates to at least one of a room status, a patient status and a bed status. The processor circuitry may be configured to execute computer-executable instructions to send via the communications interface a signal indicative of the user input to the health information system of the healthcare facility. The processor circuitry may be configured to execute computer-executable instructions to send via the communications interface a signal to a bed to cause the bed to execute an electronically-controlled bed function. The processor circuitry may be configured to execute computer-executable instructions to send via the communications interface an indication of the room status to a mobile device of a person associated with the facility. The processor circuitry may be configured to execute computer-executable instructions to send via the communications interface an indication of the room status to an output device located outside the patient's room.

According to another aspect of this disclosure, a bed system includes a bed that has a bed identifier uniquely identifying the bed to the bed system, a bed network, and a bed function controller configured to control a plurality of electronically-controllable functions of the bed by sending control signals over the bed network. The bed system also includes at least one first user control module supported by the bed and operably coupled to the bed network to enable a user to control one or more of the electronically-controllable functions of the bed, and a second user control module spaced from the at least one first user control module, spaced from the bed, electrically isolated from the bed, and operably coupled to the bed network, the second user control module comprising a housing, at least one input device supported by the housing, a display supported by the housing, memory in which data and computer-executable instructions are stored, and a processor configured to execute computer-executable instructions to cause the display to display information about the bed identified by the bed identifier, and send a signal to the bed function controller of the bed identified by the unique identifier to cause the bed function controller to execute an electronically-controlled function selected at the input device of the second user control module.

The second user control module may be in data communication with a health information system of a healthcare facility. The bed may include a built-in weigh scale, and the processor may be configured to execute computer-executable instructions to initiate zeroing of the weigh scale.

The bed may have first and second bed functions that are electronically controllable via first and second bed controls, respectively, the at least one first user control module is configured to make the first user control available for activation by a user but not the second user control, and the second user control module is configured to make the second user control available for activation by a user.

BRIEF DESCRIPTION OF THE DRAWINGS

The detailed description particularly refers to the following figures, in which:

FIGS. 10, 11A-11F, and 12 are sample screen displays for room and bed control features of a patient room and bed management system.

The same reference numbers may be used to refer to like components in the several drawings.

DETAILED DESCRIPTION

Figure 1:
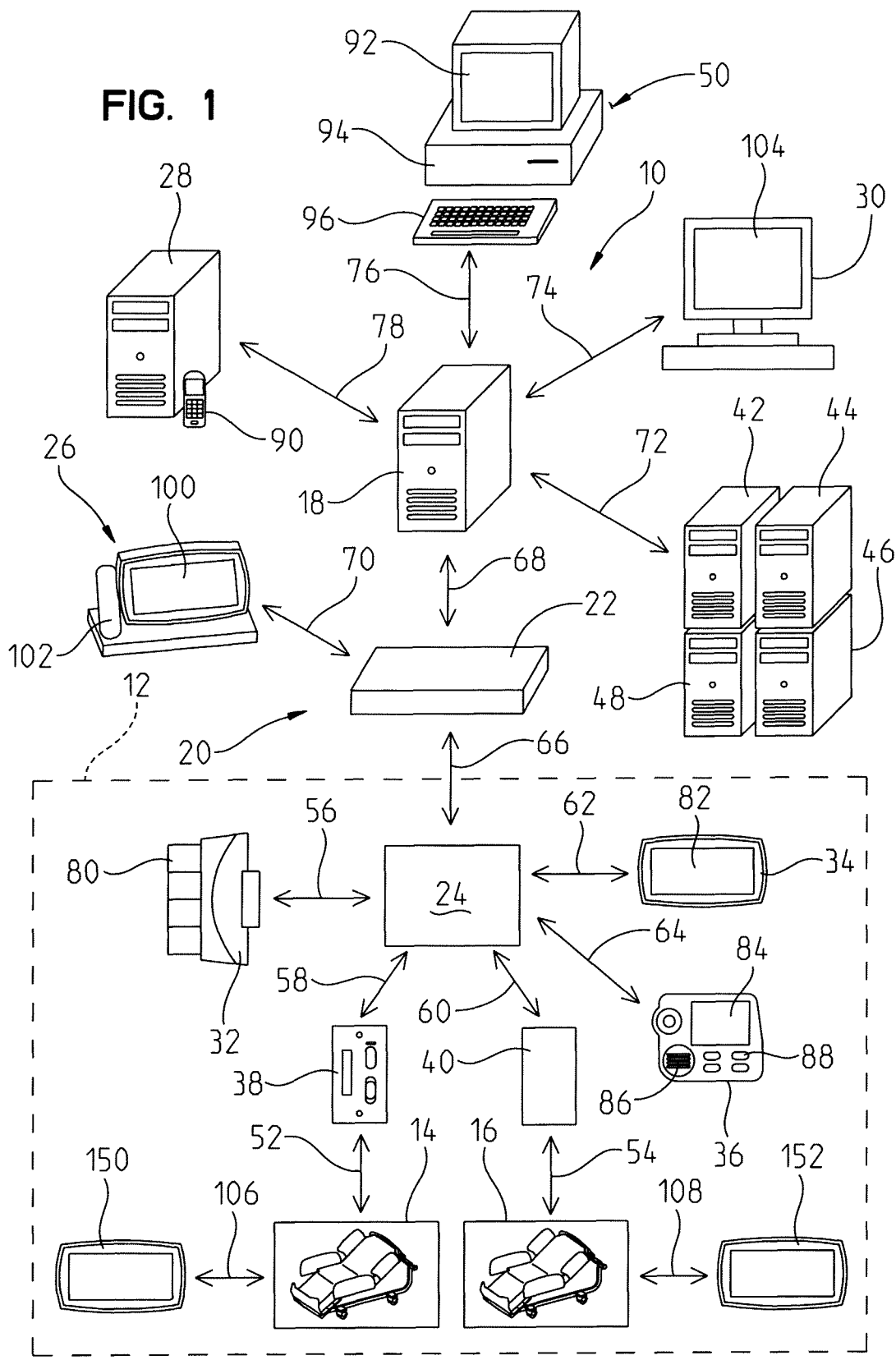
FIG. 1 is a block diagram of a portion of a computerized information and communication system for a healthcare facility equipped with patient beds.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A healthcare information and communication system 10 is typically located in a healthcare facility (such as a hospital, clinic, surgery center, or nursing home) that has a number of patient rooms 12. One or more beds 14, 16 are located in each of the patient rooms 12.

To facilitate electronic and/or telephonic communications between caregivers and other staff members of the healthcare facility, the system 10 typically has a number of non-room based components, which are located in areas of the facility outside the patient rooms (such as nurses' stations, hallways, and common areas), and a number of room-based components, which are located in or adjacent to each of the patient rooms 12.

The room-based components of the system 10 are connected to the system 10 by a communications interface 20. For clarity, only one such patient room 12 is shown in FIG. 1, however, any number of patient rooms may be linked to the system 10 in a similar fashion.

The system 10 includes a server 18. The server 18 includes computer memory, a processor or processors, computer circuitry, data and computer-executable instructions. In general, references to memory in connection with the server 18 and elsewhere in this disclosure refer to computer memory, which typically includes a combination of volatile memory (e.g. random access memory or RAM) and non-volatile memory (e.g. read-only memory such as electrically erasable programmable read-only memory or EEPROM).

In general, references to data in connection with the server 18 and elsewhere in this disclosure refer to electronic data, which typically includes information that is not variable (i.e. information that cannot be changed by a user or otherwise) and information that is variable (i.e. information that changes over time, such as sensor output, weigh scale output, or information that can be changed by a user, such as bed configuration settings). The data may be in the form of text, graphical, video or audio information stored in a digital or other electronic form. Some of the data may be stored in volatile memory, if it is not required to be saved after power to the system is turned off. Other data may be stored in non-volatile memory.

In general, references to computer-executable instructions in connection with the server 18 and elsewhere in this disclosure refer to programming code in the form of software or firmware (and may include plug-ins, applets, utilities and the like), which is typically stored in non-volatile memory. The processor or processors referred to in connection with the server 18 and elsewhere in this disclosure access data, execute the computer-executable instructions as needed and cause the functions of the system 10 to be performed via the computer circuitry. In general, the processor or processors referred to in this disclosure include one or more microprocessors or microcontrollers.

The server 18 electronically exchanges data and communications with the other components of the system 10 via a number of bidirectional communication links 68, 70, 72, 74, 76, 78. The server 18 processes data and instructions received from other system components, and electronically or telephonically routes data, communications and command or control signals to the appropriate components of the system 10 as determined through the execution of computer-executable instructions.

Some of the non-room based components of the system 10 include a network interface 22, a master station 26, a communications server 28, an electronic status board 30, and optionally, one or more other servers 42, 44, 46, 48. An HIS system 50 is external to the system 10 but interfaces with the system 10 as described herein.

The room-based components of the system 10 are in bidirectional communication with the server 18 via the communications interface 20, which includes the network interface 22, input/output circuitry 24 and communication links 66, 68. The room-based components include an indicator assembly 32, one or more patient stations 34, 36, one or more non-bed mounted user interfaces 150, 152, and bed interface units 38, 40. The room-based components 32, 34, 36, 38, 40, 150, 152 are in bidirectional communication with the input/output circuitry 24 via communication links 56, 58, 60, 62, 64.

The communication links (e.g. 56, 58, 60, 62, 64, 66, 68, 70, 72, 74, 76, 78, 106, 108) referred to herein may include a communication network such as an Ethernet network or even appropriately secured portions of the Internet. Such communication links may include wired and/or wireless links and/or combinations thereof, along with associated connectors, routers, and other components typically used in electronic communication systems.

Data and instructions communicated over the communication links (e.g. 56, 58, 60, 62, 64, 66, 68, 70, 72, 74, 76, 78, 106, 108) are formatted and transmitted according to suitable data formatting and communications protocols. For example, some data communicated by components of the system 10 is formatted according to the extensible markup language (XML) protocol. Some of the electronic communications between components of the system 10 are accomplished using the TCP/IP protocol, the RS-232 protocol, the RS-423 protocol, the RS-485 protocol, one of the IEEE 802.11x protocols (where x represents the various revision levels a, b, c, d, e, g and so forth of the 802.11 protocol), the Bluetooth protocol, the Zigbee protocol, or a mixture of protocols.

In one version of the system 10, the communication links 56, 58, 60, 62, 64, which are communication links associated with the patient room 12 that communicate data and/or instructions between devices in the patient room (e.g. 32, 34, 36, 38, 40) and the input/output circuitry 24, use the RS-485 protocol, while the links 66, 68, and 70 (i.e. the links to the network interface 22), use the TCP/IP protocol. If the TCP/IP protocol is used, some of the room-based devices, such as the patient stations 34, 36, may be connected directly to the network interface 22 without the use of the input/output circuitry 24.

For ease of discussion, this disclosure uses the term "server" to refer to computing devices that have the requisite processing power, computer memory, and other computer components to execute computer-executable instructions to provide the patient room, and bed management features described herein. Each such device may comprise one or multiple microprocessors, microcontrollers, or similar devices, or may comprise one or multiple servers that are linked via a communication network.

Healthcare facilities often have a number of organizational units, such as nursing, administration, transport, laboratory services, radiology, O/R, emergency, and environmental services or EVS (housekeeping), among others. In one version of the system 10, the "server" 18 includes a server that has a primary function of managing information and communications among caregivers (e.g. staff members associated with a nursing unit or units) and communications between caregivers and patients. The server 18 also has a secondary function of managing information and communications among staff members associated with other organizational units of the facility and managing information and communications between members of the nursing unit and members of other organizational units of the facility.

In another version of the system 10, the server 18 includes multiple servers, each of which has a primary function of managing information and communications among staff members of a specific organizational unit, as well as a server that manages information and communications exchanged between staff members associated with different organizational units. Thus, as used in this disclosure, the term "server" broadly encompasses any computing device or combination of devices that is capable of performing the functions described in this disclosure.

The computer-executable instructions referred to in this disclosure may be resident on one computing device or distributed across multiple computing devices connected by one or more communication networks. Any suitable programming code and/or framework may be used to implement the computer-executable instructions. For instance, in the illustrated version, at least some of the executable instructions are written using the C# programming language and are implemented using the .NET software development framework developed by Microsoft Corporation.

Referring first to the non-room based components of the system 10, the network interface 22 is typically a network switch, such as a Power over Ethernet (PoE) switch. Suitable network switches include, for example, the PoE switch marketed by Hill-Rom Company, Inc. in connection with its NaviCare® NurseCall™ system, and one or more of the various Dell PoE switches marketed under the PowerConnect™ brand name.

The master station 26 includes computer memory, a processor or processors, computer circuitry, and data and computer-executable instructions (e.g. software or firmware) resident in the memory (not shown). The master station 26 also includes a user interface 100 and a telephone handset 26. The user interface 100 allows users to monitor communications between staff members of the healthcare facility and between patients and staff members, monitoring electronic alerts (such as alerts received from patient beds or other patient care devices), locate staff members, route communications to appropriate staff members, manage and update the status of communications and alerts (e.g. cancel or close a call). The handset 26 enables the user to exchange voice communications with patients and/or staff members. For example, if a patient in a room presses the nurse call button, a caregiver at the master station 26 can speak directly to the patient using the handset 26.

A master station 26 can be configured to monitor multiple patient rooms, which together make up a designated zone, wing, floor or unit of the healthcare facility. The system 10 may include multiple master stations 26 (e.g. one per nursing unit), but only one master station 26 is shown in FIG. 1 for ease of discussion. The master stations 26 of different nursing units may communicate with one another by providing multiple network switches 22 that interface with each other, for example.

The communications server 28 may in practice comprise one or multiple computing devices that facilitate wired and/or wireless electronic and/or telephonic communications with remote devices such as telephones, cell phones, personal digital assistant devices (PDAs), and wireless badge-type voice communication devices such as Vocera™ badges. Whatever the type or form of communications, the server 28 is configured to translate system operations, instructions, data and communications into an appropriate message format and route the message to the appropriate endpoint.

In the illustrated version of the system 10, the communications server 28 is configured to provide voice communications capabilities using the Voice over Internet Protocol (VoIP) and the Microsoft Windows operating system. As such, it includes a soft telephony switch and other components normally associated with VoIP communications. The server 28 may also interface to the healthcare facility's facility-wide telecommunications infrastructure (e.g. a private branch exchange or PBX). In the illustrated version, the server 28 uses an Internet Protocol (IP)-based PBX such as the Microsoft 3CX Phone System, although such functionality may be performed by another server (e.g. one of the servers 42, 44, 46, 48) and/or using another type of phone system.

The electronic status board 30 is coupled to the server 18 by a bidirectional communication link 74. The electronic status board 30 has a display screen 104 and processor circuitry therewithin (not shown) configured to display current status information about multiple patient rooms 12 and/or other locations in the healthcare facility. For example, the electronic status board may display status information for all of the patient rooms in one wing, floor or unit of a healthcare facility. The status information may include, for example, an indication of whether there are any active calls or alerts for rooms in the given unit, the status of a bed or beds in the room (e.g. occupied, ready for new patient, clean, dirty), and staff assigned to the rooms in the unit. The status information may also include information about facility staff members (e.g., their current location in the facility, and whether they are active or on break, whether their rounding has been complete, etc.). The electronic status board 30 typically displays the status information for a number of the monitored locations on the display screen, all at one time, to enable staff members of the facility to quickly view the status of the monitored locations at one time, or for other reasons. One example of an electronic status board is described in U.S. patent application Ser. No. 12/711,850, which is filed on the same date herewith, and in U.S. patent application Ser. No. 12/708,950, filed Feb. 19, 2010, each of which is incorporated herein by this reference in its entirety.

Each of the servers 42, 44, 46, 48 is in electronic communication with the server 18 via appropriate communication links (e.g. link or links 72). The illustrated servers 42, 44, 46, 48 are intended to be representative of any number of additional computing devices that may optionally be connected to the system 10. For example, these servers may include a database server on which electronic medical records are stored, one or more third party servers, a user authentication server for managing user accounts, passwords, user authentication and authorization, a workflow server configured to facilitate communication with workflow software systems, a reports server configured to manage display updates and reports of calls and notifications and/or generate printed reports as may be needed for compliance with rules, procedures or standards that apply to the healthcare facility, a locating and tracking server configured to manage the locating and tracking of wireless badges or other mobile units that are linked to staff persons or equipment, a text messaging server configured to manage or facilitate the communication of text messages within the system 10, additional wireless communication servers that may be needed to manage and/or facilitate communication with specialized wireless devices, such as wireless devices that use the Emergin Wireless Office architecture, and/or other servers configured to facilitate the operation of the system 10 and/or the integration of the system 10 with third-party systems, devices, equipment or software.

The HIS system 50 is an administrative computer system used by healthcare facilities to monitor administrative tasks relating to patients and staff members. The HIS system 50 maintains information about individual patients that are admitted to the facility, transferred from one location to another within the facility, and discharged from the facility. Often, a healthcare facility staff person makes a determination of when a patient is to be admitted, transferred or discharged, and then records this information in the HIS system 50. Some examples of commercially available HIS systems include, but are not limited to, the Openlink system available from Siemens, the Cloverleaf system available from Quovadx, Inc., the EPIC system available from Epic of Verona, Wis., the STAR system available from McKesson Corp. and the Impact system available from Sybase Inc.

The HIS system 50 may generate data messages whenever the status of a patient changes, e.g. "ADT messages." For example, the data message may be "A01" if the patient has been admitted to the facility, "A02" if the patient has been transferred to a new location in the facility, or "A03" if the patient has been discharged from the facility.

The healthcare facility may use an interface engine (a software application, e.g. one of those commonly known as EPIC, Meditech, or Cloverleaf) to communicate ADT messages from the HIS system 50 to other systems that are external to the HIS system 50 but connected to the healthcare facility's network. The ADT messages are communicated electronically using the TCP/IP protocol or another suitable protocol.

In the illustrated version of the system 10, an interface engine (not shown) is provided as a part of the system 10 (e.g., is resident at the server 18). The interface engine of the system 10 is in addition to any interface engine that may be used by the healthcare facility in connection with the HIS system 50.

The interface engine of the system 10 receives ADT messages from the healthcare facility's HIS system or interface engine, as the case may be, and communicates those messages to the server 18 for use by the healthcare information and communication system 10. The illustrated version of the system 10 uses the Rhapsody interface engine available from Orion Health, which presently communicates ADT messages from the healthcare facility's HIS system 50 to the system 10 (e.g. the server 18) using the SOAP (Simple Object Access Protocol) protocol. Other versions of the system 10 may use a different interface engine or may not use an interface engine at all.

Referring next to the room-based components of the system 10, an indicator assembly 32 is typically located outside each patient room 12 in a location where it is likely to be visible by staff persons in hallways and/or common areas of the healthcare facility. The indicator assembly 32 typically has a number of independently illuminatable light panels 80. The illumination of a given light panel indicates that a change in status, condition or event has occurred in the associated patient room. The indicator assembly 32 may include a speaker and circuitry configured to output audible tones alternatively or in addition to the light panels. The indicator assembly 32 has computer circuitry (not shown) that enables bidirectional communication with the system 10 via the communication link 56 and the input/output circuitry 24. Some examples of indicator assemblies are disclosed in U.S. Patent Application Publication No. 2009/0214009.

The patient stations 34, 36 are in bidirectional communication with the system 10 via the communication links 62, 64 and the input/output circuitry 24. The patient station 34 has a graphical touchscreen user interface 82. The patient station 36 provides similar functionality to the patient station 34, but is equipped with a non-touchscreen display 84 and a series of hardpanel controls 88 (e.g. membrane switches, keys, dials or the like). The patient station 36 also has a speaker 86 and circuitry therewithin that is configured to enable direct voice communication between a staff person at the patient station 36 and a person at the master station 26. The patient station 34 also has voice communication capabilities although not shown in the drawing. Both types of patient stations 34, 36 are configured to enable a caregiver or other staff person to communicate with the system 10 (e.g. a master station 26) from within a patient room 12. As such, the patient stations 34, 36 are typically mounted to a wall or other architectural support structure in the patient room (such as a support column, headwall, or cart). The patient stations 34, 36 may also be used in staff work areas or other areas of the healthcare facility, but are referred to herein as patient stations for ease of discussion.

Typically, the patient stations 34, 36 communicate with the master station associated with their nursing unit. However, information from a patient station in one nursing unit can be communicated to another nursing unit through the nursing units' master stations using interconnected network switches as discussed above.

The input/output circuitry 24 communicates bidirectionally with the network interface 22. The input/output circuitry 24 includes computer and electrical circuitry, including a microprocessor or microcontroller and/or other electrical components as needed, to facilitate two way electrical communications between the room-based components of the system 10 and the network interface 22. The input/output circuitry 24 is typically arranged on a printed circuit board assembly. In some versions of the system 10, the input/output circuitry 24 is installed in a housing, which may be located adjacent the indicator assembly 32 associated with a patient room 12.

The beds 14, 16 are typically hospital beds, stretchers or other patient support structures that have one or more electronically-controlled bed functions. In the illustrated version of the system 10, the beds 14, 16 have a built-in weigh scale, that is, a feature whereby a patient's weight can be obtained while the patient is on the bed. The built-in weighing feature is electronically activated, e.g. by a caregiver pressing a button on the bed's graphical user interface.

In order for the bed's built-in weigh scale to work properly, it must be zeroed prior to placing the patient on the bed. Additionally, other conditions may need to be met in order to obtain an accurate patient weight using the bed-integrated weigh scale (i.e. the bed must be in the same state each time the patient is weighed). For example, the bed may need to be in a certain position or have certain items placed on it or removed from it (such as extra bed sheets or a blanket) in order to be properly zeroed. If the bed-integrated weigh scale is not properly zeroed, the patient may need to be weighed using a traditional lift scale or lift sling. Additional time may be required, and/or additional staff persons may be needed, to lift the patient onto the lift scale or sling. The bed-integrated weigh scale aims to eliminate the need for a caregiver to use a traditional lift scale or lift sling to weigh the patient.

Some of the beds 14, 16 are equipped with sensors that are configured to detect certain conditions of the bed. For example, some beds have position sensors (such as force sensors) that detect force applied to the bed at different locations on the bed. The bed controller 192 includes computer-executable instructions that determine, based on the output of the force sensor or sensors, the position of a patient relative to the bed (e.g. the patient has exited the bed, is on the edge of the bed, or is sitting up in bed). The bed controller 192 may then issue a visual and/or audible signal and/or communication signal relating to the patient's position.

Some of the beds 14, 16 are equipped with orientation sensors, such as ball switches, potentiometers, inclinometers or accelerometers, which detect changes in the orientation of the bed or one section of the bed relative to another section of the bed. For example, an orientation sensor may be used to determine the angle of the head section or the foot section of the bed relative to the bed frame or to the horizontal. The bed controller 192 includes computer-executable instructions that determine, based on the output of the orientation sensor or sensors, the orientation of the bed. The bed controller 192 may then issue a visual and/or audible signal and/or communication signal relating to the bed's orientation.

Some of the beds 14, 16 are equipped with pressure sensors, such as transducers, strain gauges, capacitive, optical or piezoelectric sensors, which detect changes in pressure inside air bladders of the bed's mattress (if the bed's mattress has air bladders). The bed controller 192 includes computer-executable instructions that determine, based on the output of the pressure sensor or sensors, the pressures within air bladders or zones of air bladders of the bed's mattress. The bed controller 192 may then determine that a bed condition has occurred based on the pressure sensor output, such as a bottoming out condition or a max-inflate condition. The bed controller 192 may alternatively or in addition issue control signals to inflate or deflate certain air bladders based on the output of the pressure sensors, as may be the case when the bed is operating in an automatic pressure relief mode or a therapy mode. The bed controller 192 may issue a visual and/or audible signal, and/or communication signal relating to the mattress condition or status.

The sensors with which the beds 14, 16 are equipped may output data signals in discrete or continuous, analog or digital form. The beds 14, 16 are equipped with appropriate signal processing circuitry and/or devices (e.g. analog-to-digital converters, digital-to-analog converters, filters, and the like) to enable the bidirectional communication of signals between the sensors and the bed controller.

Figure 2A:
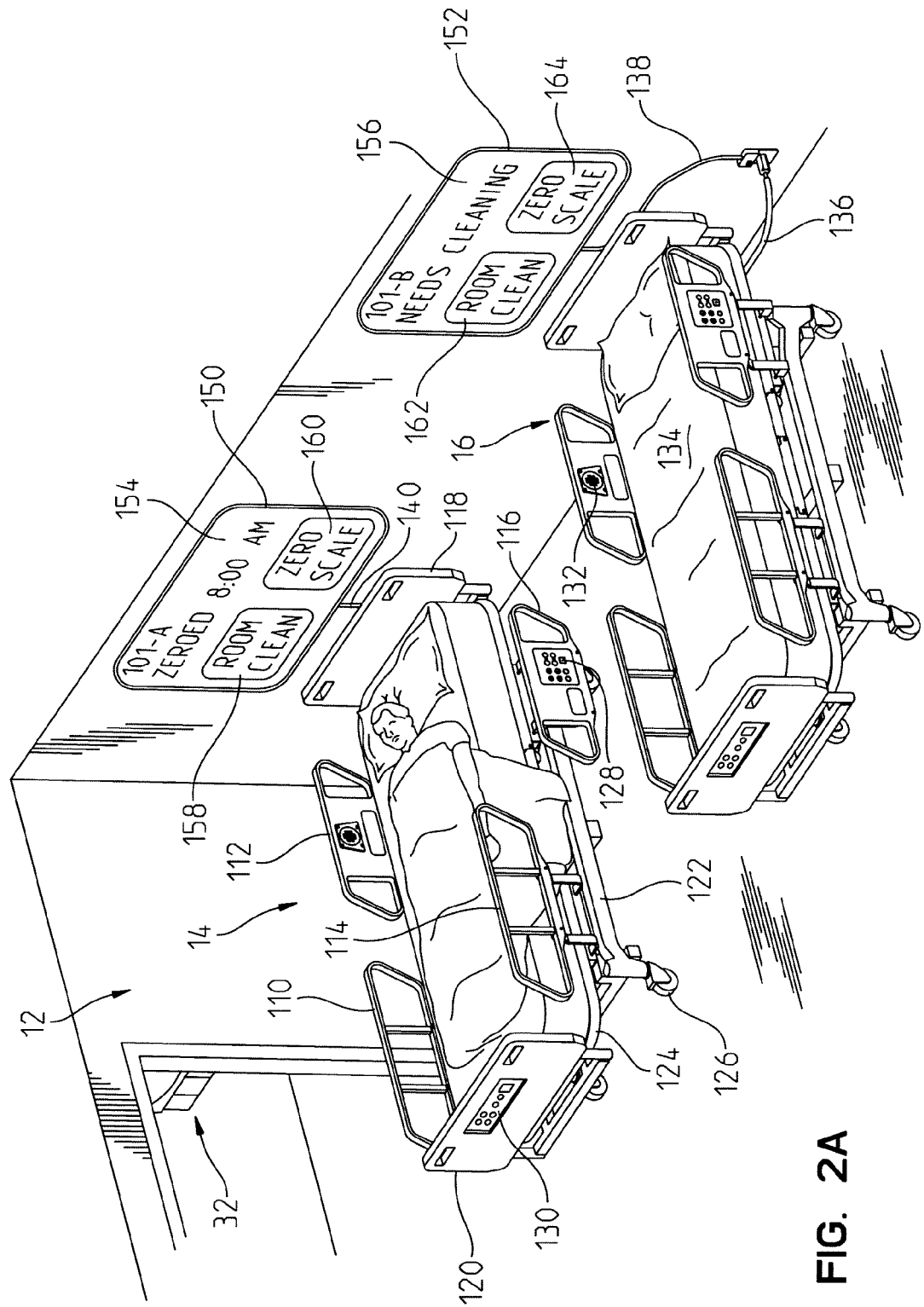
FIG. 2A is a perspective view of a patient room including patient beds with bed-mounted user controls and non-bed mounted user interfaces.

As shown in FIG. 2A, each of the beds 14, 16 has a frame 122, a deck 124 supported by the frame, a number of wheels 126 movably supporting the frame 122, and a patient support surface 134 (e.g. a mattress) supported by the deck 124. The deck 124 typically has a number of articulating deck sections including at least a head section and a foot section. Some configurations of the deck 124 have a back section, a seat section and/or a thigh section in addition to the head and foot sections.

Around the perimeter of the beds 14, 16 are a headboard 118, a footboard 120, a pair of siderails 112, 116 located nearer to the head end of the bed, and a pair of siderails 110, 114 located nearer to the foot end of the bed. Some or all of these components may be attached to a portion of the frame 122 or the deck 124. The siderail 116 of the bed 14 is shown in a lowered position, while the other siderails are shown in a raised position.

Each of the beds 14, 16 has a number of on-board user control modules 128, 130, 132. The user module 128 is supported by a panel of the siderail 116 that faces outwardly away from the patient. The user module 130 is supported by a panel of the footboard 120 that faces outwardly away from the patient. The user module 132 is supported by a panel of the siderail 112 that faces inwardly toward the patient.

The user modules 128, 130 typically enable a caregiver to control a number of electronically-controlled functions of the bed 14, 16, such as weighing the patient, raising and lowering the head section, placing the bed into a Trend, reverse Trend, high, low, or "chair" position (e.g. pivoting the foot section to a position in which the foot section of the deck is at an angle relative to the bed frame), starting or stopping a mattress therapy (such as rotation, turning assistance, or percussion and vibration), setting or canceling a head of bed angle alert or bed exit alert, and/or adjusting pressure in one or more sections of the mattress.

The user module 132 typically allows the patient to activate or deactivate certain bed functions, such as raising and lowering the head section of the bed. The user module 132 typically does not include functions that are normally only performed by an authorized caregiver (such as starting and stopping therapies, weighing the patient or configuring alerts). A nurse call button is also usually provided on the user module 132.

Each of the beds 14, 16 is connected to a supply of electrical power (e.g. by a power cord 136). Some examples of patient care beds that can be used in connection with the system 10 include the TotalCare® bed, the CareAssist® bed, and the VersaCare® bed, which are available from the Hill-Rom Company, Inc.

Each of the beds 14, 16 are typically connected to the system 10 by a bed connector unit 38, 40 and bidirectional communication links 52, 54. The bed connector units 38, 40 enable data and computerized instructions to be communicated between the beds 14, 16 and the system 10. The bed connector unit 38 includes a serial peripheral interface (SPI) link, such as a 37-pin connector to a 37-pin bed cable. The bed connector unit 40 is another version of a bed connector commonly referred to as a "Silver Plate" connector, where "silver" refers to the color of the device, not its function or composition). In general, the bed connector units 38, 40 are any suitable mechanism that is configured to facilitate a wired or wireless electronic connection between the beds 14, 16 and the room-based input/output circuitry 24.

In the version of the system 10 illustrated in FIGS. 1 and 2A, each of the beds 14, 16 has a non-bed mounted user interface 150, 152 connected thereto via a bidirectional communication link 106, 108. The non-bed mounted user interfaces 150, 152 each include a display 154, 156 as well as one or more user controls 158, 160, 162, 164.

The non-bed mounted user interfaces 150, 152 may each be configured to control room-related functions of the system 10 as well as specific functions of an associated bed and/or other medical equipment or devices located in the room 12. The non-bed mounted user interface 150 has a display screen 154 and one or more user controls 158, 160. The user interface 150 is connected to a power supply by a cord 140. Similarly, the user interface 152 has a display screen 154 and one or more user controls 162, 164.

Computer circuitry within the non-bed mounted user interfaces 150, 152 detects an identifier of the associated bed 14, 16 (or other device or equipment located in the room) sent to the user interface 150, 152 over the communication link 106, 108. The user interface 150, 152 displays information relating to the bed, device, or equipment, and the room, on the display screens 154, 156. The identifier may be a unique identifier such as a serial number, or a non-unique identifier, such as a bed type identifier (e.g. the make or model of the bed).

For example, in the illustrated version, the non-bed mounted user interfaces 150, 152 each receive a signal from their associated beds when the bed's built-in weigh scale is zeroed. The signal may include data associated with the zeroing of the weigh scale (e.g. a date and time stamp). The user interface 150, 152 displays this information on the display 154, 156.

Additionally, the non-bed mounted user interfaces 150, 152 receive data from the system 10 indicating whether the room or portion of the room in which the bed is located needs to be cleaned or has been cleaned, and displays this information on the display 154, 156. There are a number of possible ways by which the system 10 makes the association of a patient bed with a particular room. In one version of the system 10, the bed connector unit 38, 40 or the non-bed mounted user interface 150, 152, 166 has a location identifier associated with it. The location identifier is transmitted to the system 10 when the bed is connected to the bed connector unit or the non-bed mounted user interface. The system 10 has a database or look-up table in which data is stored that associates the location identifiers with their respective locations (e.g. patient rooms, locations within the patient rooms, or other locations in the facility). When the system 10 receives a location identifier signal, it determines the location of the bed by accessing the database or lookup table of location identifiers and locations. The system 10 may then link the location identifier with the bed identifier until the system 10 receives a signal that indicates that the bed has moved to a new location (e.g. the bed has been connected to a different bed connector unit or non-bed mounted user interface).

In another version of the system 10, a database or lookup table is maintained that maps bed identifiers directly to location identifiers. In this version, the data may be manually entered into the database or lookup table as beds are assigned to locations. In still another version, the beds are equipped with locating and tracking tags (e.g. tags that emit infrared signals). When a bed is moved to a location, an infrared receiver at that location (e.g. at a patient station, non-bed mounted user interface, or bed connector unit) detects the infrared signal and sends a location signal to the system 10. The system 10 then updates the bed location information in the database or lookup table.

On the non-bed mounted user interfaces 150, 152, the user controls 158, 162 allow a user to indicate to the system 10 that the bed or associated room is clean and ready for a new patient, rather than requiring the person to locate the nearest patient station or master station (e.g. 26, 34, 36). The user controls 160, 164 allow a user to zero the bed's weigh scale directly from the non-bed mounted user interface 150, 152 rather than requiring the user to locate and use one of the bed-mounted controls (e.g. 128, 130).

Computer circuitry at the user interface 150, 152 may selectively activate or deactivate certain user controls, based on the current status or condition of the associated bed or the room in which the bed and the user interface are located. For example, if the system 10 has received data indicating that the room in which the bed is located has already been cleaned, or if the bed is currently occupied, then the "room clean" icon 158, 162 may be omitted from the display.

Figure 2B:
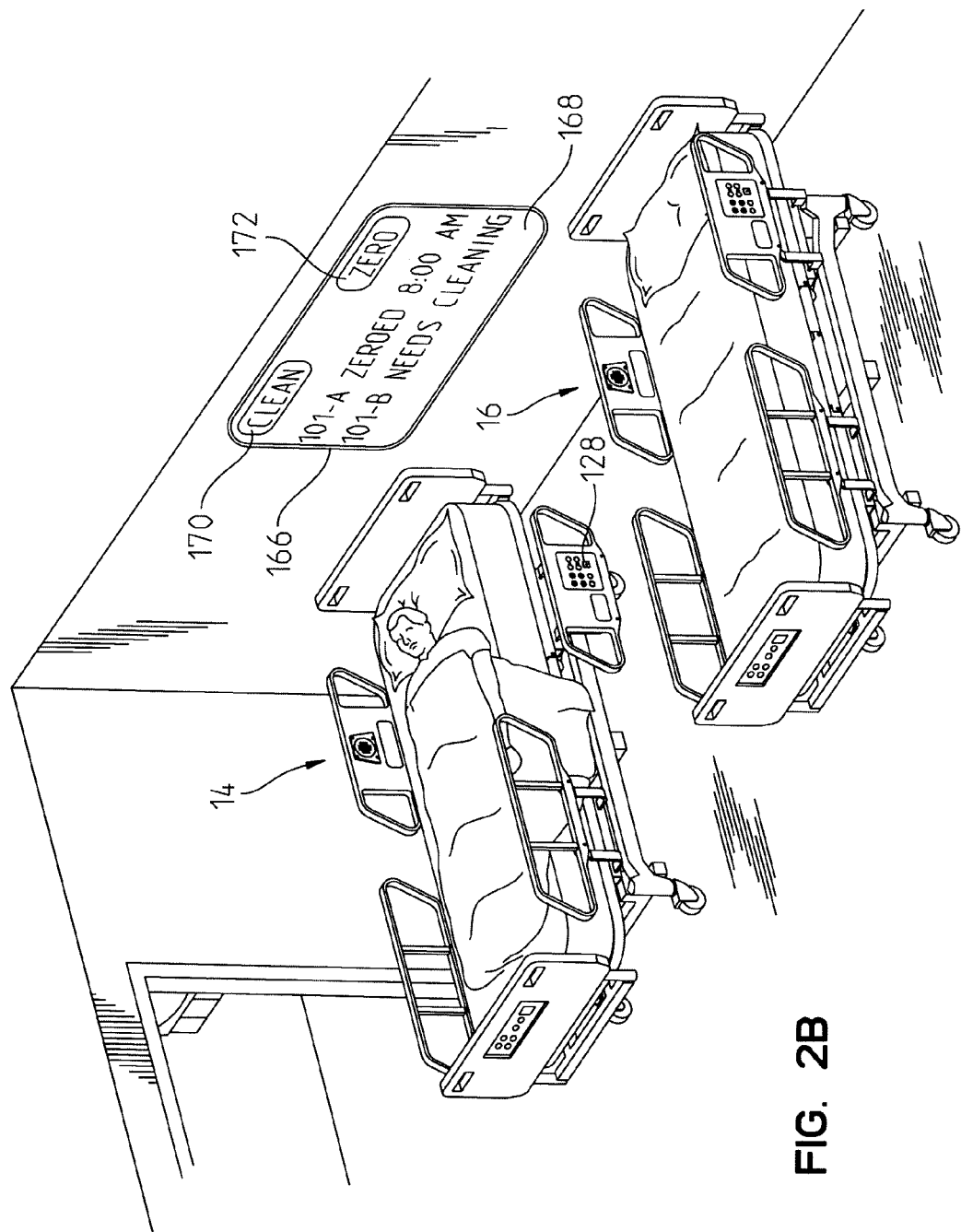
FIG. 2B is a perspective view of a patient room including patient beds and another version of a non-bed mounted user interface.

In FIG. 2B, another version of a non-bed mounted user interface 166 is shown. The non-bed mounted user interface 166 has internal circuitry configured to receive and manage data from both of the beds 14, 16, to send command or control signals to either of the beds, and to communicate with the system 10. The non-bed mounted user interface 166 may identify the beds and their locations using bed identifiers and location identifiers according to one of the methods described above.

The non-bed mounted user interface 166 includes a display 168 and one or more user controls 170, 172. Information about the status of each of the beds 14, 16 is received from the beds and is displayed on the display 168. A user control 172 enables a staff person to zero the weigh scale of the associated bed directly from the non-bed mounted user interface 166 rather than requiring the person to locate and use one of the bed-mounted controls (e.g. 128, 130). Another user control 170 enables a staff person to indicate that the bed or the room has been cleaned directly from the non-bed mounted user interface 166 rather than requiring the person to locate the nearest patient station or master station (e.g. 26, 34, 36).

Other bed controls may be provided on the non-bed mounted user interfaces 150, 152, 166, alternatively or in addition to those described above. For example, other bed features and functions that may be accessed, viewed, and/or controlled from the non-bed mounted user interface 150, 152, 166 include, but are not limited to: configuring, setting or canceling alerts or audible alarms (such as patient position, head of bed angle, brake not set, and siderail down alerts or alarms), viewing or changing the bed's position, orientation, mode or status (e.g. high or low bed height, chair, Trend, reverse Trend, CPR mode, normal or battery power mode, pressure relief mode, percussion, vibration, or rotation therapy mode, turn assist mode, maxinflate mode, sleep mode, heel pressure relief mode, viewing the bed's head of bed angle or a history of the head of bed angle over time, viewing the status of the bed's weigh scale (e.g. zeroed or not zeroed), viewing a patient's weight history or history of therapy, clearing history information, viewing an indication of the position of the bed's brake, turning on or off a bed status indicator light or "SafeView" light, and/or viewing an indication of whether the bed is connected to a healthcare facility network.

Other room-based or non-bed related controls may be provided on the non-bed mounted user interfaces 150, 152, 166, alternatively or in addition to those described herein. For example, other features and functions that may be accessed, viewed, and/or controlled from the non-bed mounted user interface 150, 152, 166 include, but are not limited to: sending a call to the healthcare facility's nurse call system, receiving a call from the healthcare facility's nurse call system, entering the status or location of a caregiver or other staff person (e.g. on duty, on break, rounding, round completed, etc.), viewing and/or updating a patient's medical chart, viewing or updating a patient's status (e.g. admit, transport, discharge), issuing a request for patient transport, adjusting the volume of a radio, television or other media device located in the room, turning on or off or adjusting the level of lighting in the room, turning on or off or adjusting a reading light, turning on or off or adjusting a night light, and/or turning a visual or audible indicator on the room's indicator assembly (e.g. 32) on or off.

In general, the combination of bed and room-based or non-bed features on the non-bed mounted user interface (150, 152, 166) simplifies the staff person's tasks as all relevant tasks can be controlled from one user interface at one location inside the patient's room, rather than from multiple user interfaces positioned at multiple locations in the facility.

In the illustrated versions of the non-bed mounted user interfaces 150, 152, 166, the displays 154, 156, 168 are touch-sensitive panels, such that the user controls 158, 160, 162, 164, 170, 172 may be activated and/or deactivated by touching the display in the area of the user control. In other versions of the non-bed mounted user interfaces 150, 152, 166, any of the user controls may be configured as hardpanel controls (such as keys, buttons, membrane switches, dials, or the like) or may be voice-activated, and a non-touchscreen display may be used in place of the touchscreen display.

In the illustrated version, the non-bed mounted user interface 166 is configured to enable a staff person to select the particular room/bed of interest (e.g. 101-A or 101-B) by touching the screen in the area of the desired room-bed identifier. For instance, if the user touches the "101-A" area of the display 168, and then presses the "zero" button 172, then circuitry within the non-bed mounted user interface 166 will change the display (e.g. "highlight" the "101-A" area of the display 168), identify the bed via a stored identifier for the 101-A bed, and send a command or control signal to the 101-A bed's controller 192 to zero its weigh scale. The built-in weigh scale of the bed 101-A will then be zeroed by the internal bed controller 192.

The bed identifier may include information that uniquely identifies a particular bed, such as a serial number. The bed identifier may alternatively or additionally include information that uniquely identifies the bed by its location in the room, i.e. a unique number or code identifying the bed interface unit, non-bed mounted user interface, or communications port to which the bed is connected in the room. Additionally, the bed identifier may include information that identifies the type of bed (e.g. make, model, and/or configuration).

Each of the non-bed mounted user interfaces 150, 152, 166 is configured to be easier to locate, access and view by a staff person than the bed-mounted user interfaces 128, 130. The illustrated versions of the non-bed mounted user interfaces 150, 152, 166 are configured to be mounted to a wall or other architectural structure in the patient room 12 (such as a headwall, support column, cart or table).

The illustrated non-bed mounted user interfaces 150, 152, 166 have a larger viewing area and higher resolution than other bed and healthcare system user interface control modules, although the non-bed mounted user interfaces 150, 152, 166 may be any size. For example, in one version, the non-bed mounted user interfaces 150, 152, 166 have a display area that is in the range of about two times (e.g. 1280×768 pixels) larger than either the bed-mounted user interfaces 128, 130 or the patient stations 34, 36. The non-bed mounted user interfaces 150, 152, 166 are also configured to be easier to maintain and keep clean than the bed-mounted mounted user interfaces 128, 130.

In some versions of the system 10, the non-bed mounted user interfaces 150, 152, 166 include computer circuitry that customizes the display and the configuration of user controls based on information received from the bed. For instance, if the user interface 150, 152, 166 determines (e.g. based on the bed identifier data received from the bed) that the bed is of a type that does not have its own (i.e. bed-mounted) graphical user interface (one example is the CareAssist™ bed available from the Hill-Rom Company, Inc.), then the non-bed mounted user interface 150, 152, 166 may display a greater amount of information and/or provide a larger number of user controls than if the bed is determined by the user interface circuitry to be of a type that does have its own on-board graphical user interface (one example is the TotalCare® bed available from the Hill-Rom Company, Inc.). In some versions of the system 10, the user interface 150, 152, 166 is configured to provide all of the functionality typically provided by the bed-mounted graphical user interface, in which case the bed-mounted graphical user interface may be removed or omitted from the bed.

In other versions of the system 10, the control of bed functions may be split between the bed-mounted user interface and the non-bed mounted user interface. For instance, the non-bed mounted user interface 150, 152, 166 may be configured to provide some of the functionality traditionally provided by the bed-mounted graphical user interface but which is only typically usable while the bed is stationary or located in a patient's room (such as mattress features like percussion and vibration or rotation, and patient position monitoring alarms).

In some versions of the system 10, the bed-mounted user interface may provide certain "generic" functionality, such as features that are usable both when the bed is stationary and when the bed is in transit (e.g. as bed positioning controls, statistics reports, and service or maintenance related functions), while the non-bed mounted user interface may provide functionality that is primarily usable when the bed is located in a patient room or generally not used or usable when the bed is out of the patient's room or is in transit, and/or functionality that requires the user to perform multiple actions at the user interface (such as configuring a bed exit alert or setting a schedule for rotation or pulmonary therapy), and/or functionality that requires a more complicated display (e.g. text and graphics, such as viewing a patient's weight history or therapy history). Thus, in some versions of the system 10, certain functionality may be eliminated from the bed-mounted user interface, which may simplify or reduce the complexity and/or cost of the bed-mounted user interface.

As shown in FIG. 1, the non-bed mounted user interfaces 150, 152, typically communicate directly with the associated beds 14, 16 rather than through an interface that involves multiple components (e.g. bed connector units 38, 40 and input/output circuitry 24).

Figure 3:
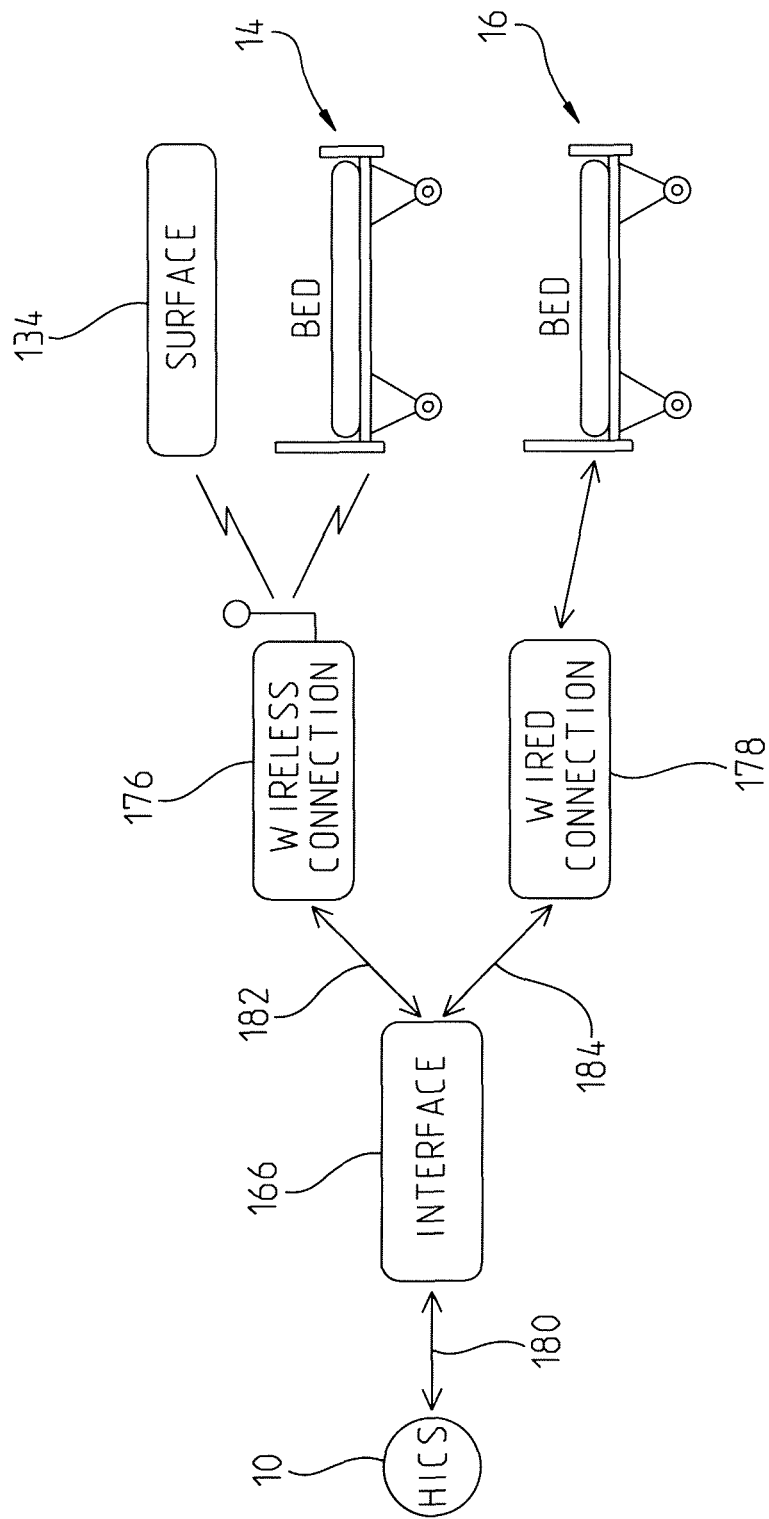
FIG. 3 is a schematic diagram illustrating network connections between patient beds and a healthcare information and communication system.

Referring to FIG. 3, the non-bed mounted user interface 166 is capable of communicating with multiple beds 14, 16 and/or other equipment or devices, via wired or wireless links 182, 184. To accomplish this, the non-bed mounted user interface 166 has a number of communication ports (e.g. RS-232, USB, or the like), where the number of communication ports relates to the number of beds or other devices that can be connected to the non-bed mounted user interface 166 at the same time.

The non-bed mounted user interfaces 150, 152, 166 may communicate bidirectionally with the system 10 by connecting to a network interface 22 or 180, which connects to the healthcare facility's communication network. The network interface 180 may include a connection to a network interface 22 (e.g. a PoE switch), or may connect to the server 18 directly (e.g. via a serial link) using one of the communication protocols described above.

FIG. 3 illustrates schematically that the beds 14, 16 in the patient room 12 may be connected to the non-bed mounted user interface 166 by either wired 176 or wireless 178 connections, depending on the configuration of the non-bed mounted user interface 166 and the beds 14, 16.

Also, a particular patient support surface 134 used with a bed (e.g. bed 14), and/or other devices or equipment in the room, may have wireless communication capabilities, and may communicate with the same wireless access point as the bed 14. In such event, the surface 134 (or other device or equipment) and the bed 14 typically have wireless communication circuitry that operates independently of the other (e.g. using different frequencies and/or transmission times). Thus, the non-bed mounted user interface 166 may be configured to communicate with one bed (and/or surface) via a wireless connection and also with another bed via a wired connection, while both of the beds are located in the same room or each of the beds is located in a different room.

Figure 4:
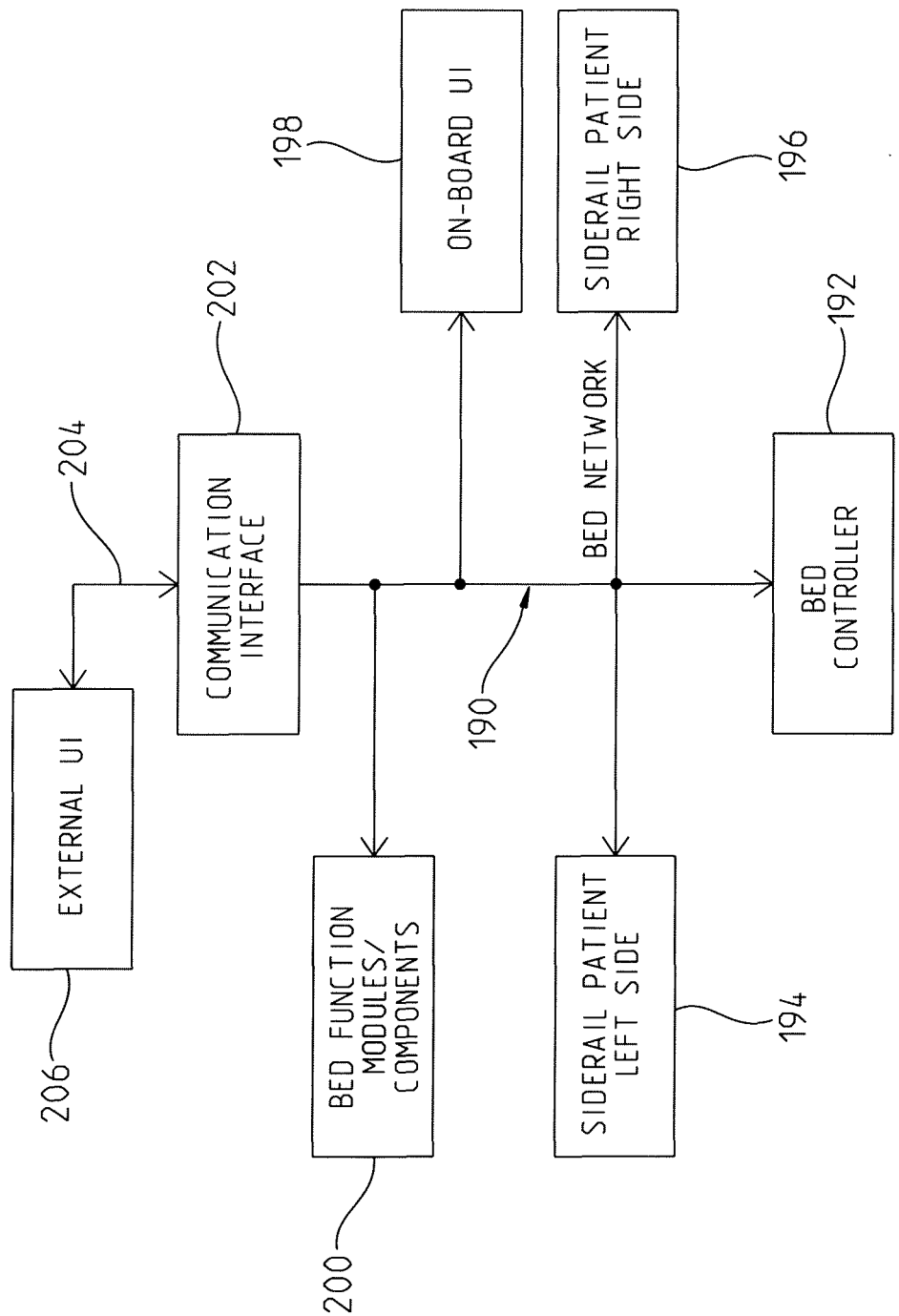
FIG. 4 is a schematic diagram illustrating a non-bed mounted user interface and a bed-mounted user interface connecting to the bed controller via an internal bed network.

FIG. 4 schematically illustrates one configuration wherein the non-bed mounted user interface 150, 152, 166 is electrically isolated from but is in communication with the bed's internal bed control network (e.g. either as a node on the bed network or as isolated from the bed network). For ease of discussion, in FIG. 4, the schematic element 202 (external user interface) is used to refer generally to any of the non-bed mounted user interfaces 150, 152, 166 that may be in communication with a bed to control bed functions yet are not mounted to the bed. Similarly, the schematic element 198 (on-board user interface) is used to refer generally to any of the bed-mounted user interfaces 128, 130, 132.

As discussed above, some beds that have a number of electronically-controlled functions have an internal bed network 190 that connects computerized functional modules or electromechanical components of the bed 200 to the bed's internal bed function controller 192. In general, the bed function controller 192 receives data and/or instructions from functional modules or bed components 200 that are connected to the network 190, and sends data and/or instructions to functional modules or components of the bed 200 to perform the electronically-controlled bed functions.

The bed function controller 192 has nonvolatile memory in which bed function settings are stored. The bed function controller 192 sends the current bed function settings to the bed-mounted user interface 198 and the non-bed mounted user interface 206 via the bed network 190, which display the current settings and provide user controls to allow the settings to be changed by a user.

If a user changes a setting at one or the other of the user interfaces 198, 206, the newly input settings are briefly stored in local memory at the user interface 198, 206 at which the settings were entered, and then the settings are sent by the user interface 198, 206 to the bed controller 192 via the bed network 190. The bed controller 192 verifies that the requested settings are within a valid range and sends a signal back to the user interface 198, 206 to confirm that the new settings have been accepted. Once the bed controller 192 has confirmed the new settings, all of the user interfaces 198, 206 are updated with the new settings. If the bed controller does not validate the requested settings, the user interfaces 198, 206 will display a message and if a bed function is in progress, the function may be canceled.

Either of the user interfaces 198, 206 may be configured to accept binary input, such as turning a bed function on or off. For binary input, the user interfaces 198, 206 associate an identifier identifying the source of the input (e.g. one of the user interfaces 198, 206). If one of the user interfaces 198, 206 accepts binary input, the bed controller 192 will activate or deactivate the associated bed function in accordance with the input.

If input is received at one of the user interfaces 198, 206, then conflicting input is received at another of the user interfaces 198, 206, then the bed controller 192 will accept the last input received and ignore any conflicting inputs received prior to the latest-in-time of the inputs received.

In the illustrated version, each of the beds 14, 16 has a pair of head-end siderails 112, 116. Each of the siderails 112, 116 has a user control module 128, 132, which includes one or more non-GUI user controls (such as hardpanel controls). These user controls are represented schematically in FIG. 4 by elements 194 (siderail patient left side controls) and 196 (siderail patient right side controls). Electrical signals issued by the siderail controls 194, 196 are communicated to the bed controller 192 via the bed network 190. The bed controller 192 then sends command or control signals over the bed network 190 to cause the requested action to occur.

For instance, if a "head up" button is pressed at one of the siderail modules 194, 196, a head up request signal is sent to the bed controller 192 over the network 190. The bed controller 192 then sends a "head up" control signal to the appropriate bed function module or electromechanical component of the bed 200 (e.g. a head section actuator) to raise the head section of the bed. The module or component 200 may send a signal to the bed controller 192 via the network 190 to confirm receipt of the control signal, to indicate that the requested operation has been completed, or to indicate that an error condition has occurred or that the requested operation cannot be performed for some other reason.

The non-bed mounted user interface 206 is electrically isolated from the bed network 190 (and the bed frame) by a communication interface 202. In addition to being electrically isolated from the bed network 190, the non-bed mounted user interface 206 may either be connected to the bed's internal network 190 (e.g. be a "node" on the bed network 190), or may be isolated from the bed network 190.

In either configuration, the bed network 190 sends bed-specific information (such as the bed type, model and/or configuration) to the non-bed mounted user interface 206, via the communication interface 202 and bidirectional communication link 204, upon detecting that the non-bed mounted user interface 206 is connected.

Computer circuitry of the non-bed mounted user interface 206 processes the bed-specific information and configures the screen display and user controls according to the particular features and installed options of the detected bed. For instance, if the non-bed mounted user interface 206 determines that the bed does not have a graphical user interface installed on it (i.e. mounted to the bed), then the non-bed mounted user interface 206 will configure itself to provide a graphical user interface to control the electronically-controlled functions of the bed.

If the non-bed mounted user interface 206 is isolated from the bed network 190, the non-bed mounted user interface 206 interfaces to a network adapter board at the communication interface 202 of the bed. The network adapter (not shown) provides electrical isolation of the non-bed mounted user interface 206 from the bed. The network adapter includes hardware and/or software and/or firmware that provides a "generic" means by which the non-bed mounted user interface 206 communicates with the bed network 190.

Some beds use a network configured according to the Controller Area Network (CAN) protocol, while other beds use an Echelon communications protocol. Also, some user interfaces 206 may be configured to communicate via one or the other of the CAN or Echelon protocols.

Aspects of the system 10 may be configured to operate with either type of protocol using a network bridge. The network bridge provides the requisite hardware, software, and/or firmware to enable the non-bed mounted user interface 206 to communicate with bed networks independently of the protocol used by the network. As such, one non-bed mounted user interface 206 may be used with a number of different beds.

One example of a network bridge is a bridge board that is a CAN node at the communication interface 202. The bridge board sends and receives CAN network information out to the non-bed mounted user interface 206 via a serial (e.g. UART) port.

"Electronic isolation" generally refers to the ability to connect two devices safely with appropriate clearance and creepage. For electrical isolation, a wireless transmission such as an optical link (e.g. fiber optic or infrared) from the bridge board to the non-bed mounted user interface 206 may be used. Fiber optic communications use a glass or plastic fiber, a connector, and a transceiver to enable wireless data communications between the non-bed mounted user interface 206 and the bed network 190. The fiber optic cable provides the necessary electrical isolation. Suitable fiber optic cables, connectors and transceivers are widely commercially available from Avago (e.g. part numbers HFBR-1521Z transmitter and HFBR-2521Z receiver), and/or other suppliers, and include fiber optic Ethernet.

Infrared data communications require a line of sight connection (i.e. since infrared signals cannot penetrate walls or other structures), with a typical range of one meter and a thirty-degree cone-shaped beam. Suitable infrared transceivers are available from Vishay (e.g. Vishay VFIR 16 Mbit/sec, FIR 4 Mbit/sec, or SIR 115.2 kbit/sec). One suitable infrared controller is the RPM972-H14 IrDA infrared communication module available from Rohm.

Since the infrared signal travel through the air, the non-bed user interface 206 is electrically isolated from the bed. The line-of-sight communication of infrared communications can be advantageous since the infrared signals will not bleed into adjacent rooms. Thus, the infrared communication technology can be used to determine whether a bed (or other device or equipment) is located in a particular room.

If the non-bed mounted user interface 206 is a node on the bed network 190, then electrical isolation is provided by an internal barrier such as an isolated transceiver. An electrical cable couples the non-bed mounted user interface 206 to the bed network 190 at the communication interface 202. The isolated transceiver can be a discrete component or an integrated circuit. One example of a suitable isolated transceiver is the isolated CAN transceiver known as Part No. ISO1050 made by Texas Instruments.

Electrical isolation of the non-bed mounted user interface 206 from the bed enables the non-bed mounted user interface 206 to utilize its own power supply, independently of the bed's power supply, and also enables the non-bed mounted user interface 206 to connect to other equipment, devices and/or networks within the facility independently of the bed.

FIGS. 5A-5D schematically illustrate side views of different alternative configurations for establishing wireless communication between a bed (e.g. beds 14, 16) and a non-bed mounted user interface (e.g. 150, 152, 166). In these figures, for ease of discussion, the reference numeral 210 is used to generically refer to any of the beds 14, 16 that may be connected to a non-bed mounted user interface 206.

Figure 5A:
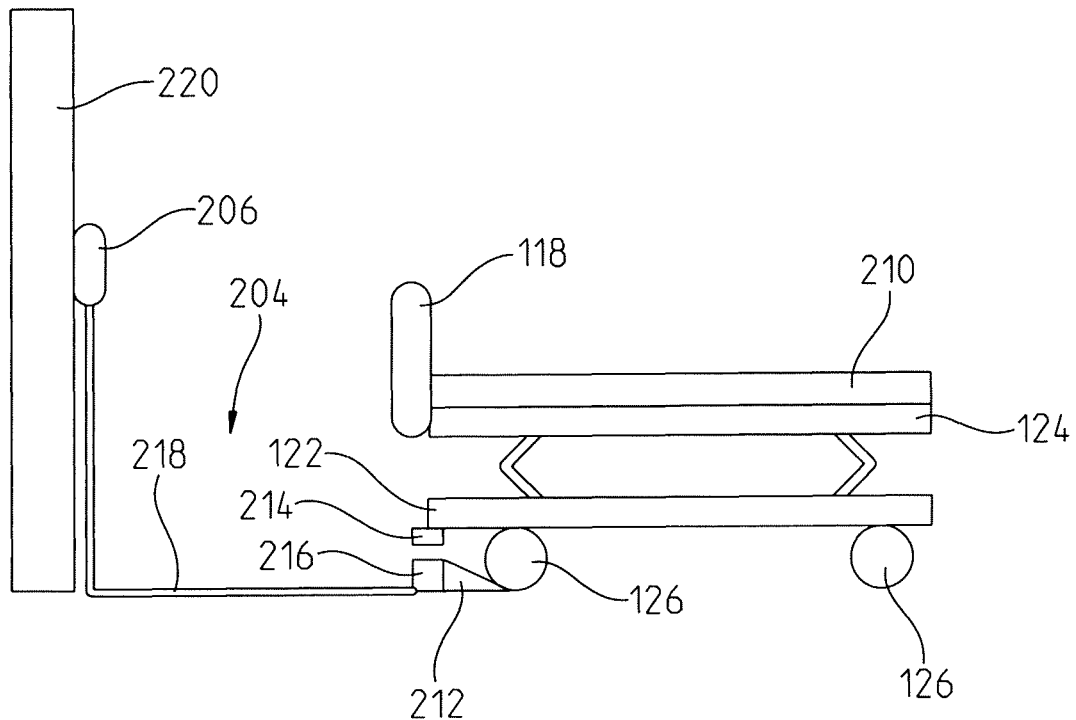
FIGS. 5A-5D are schematic diagrams illustrating a number of configurations for connecting a patient bed to a non-bed mounted user interface.
Figure 5B:
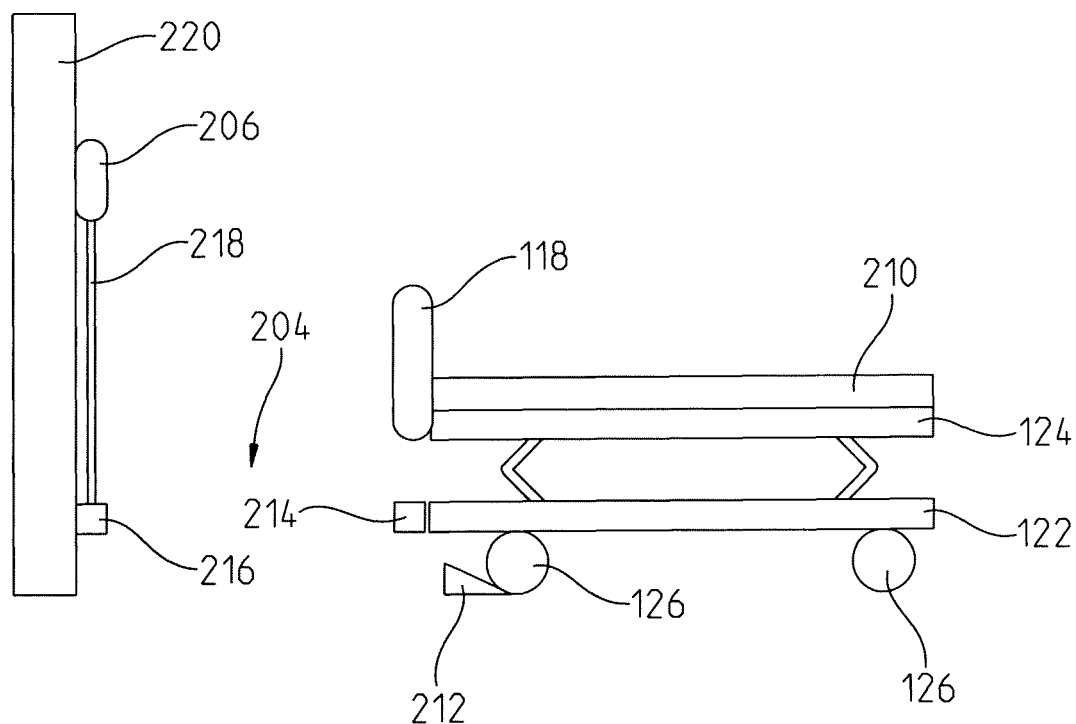
Figure 5C:
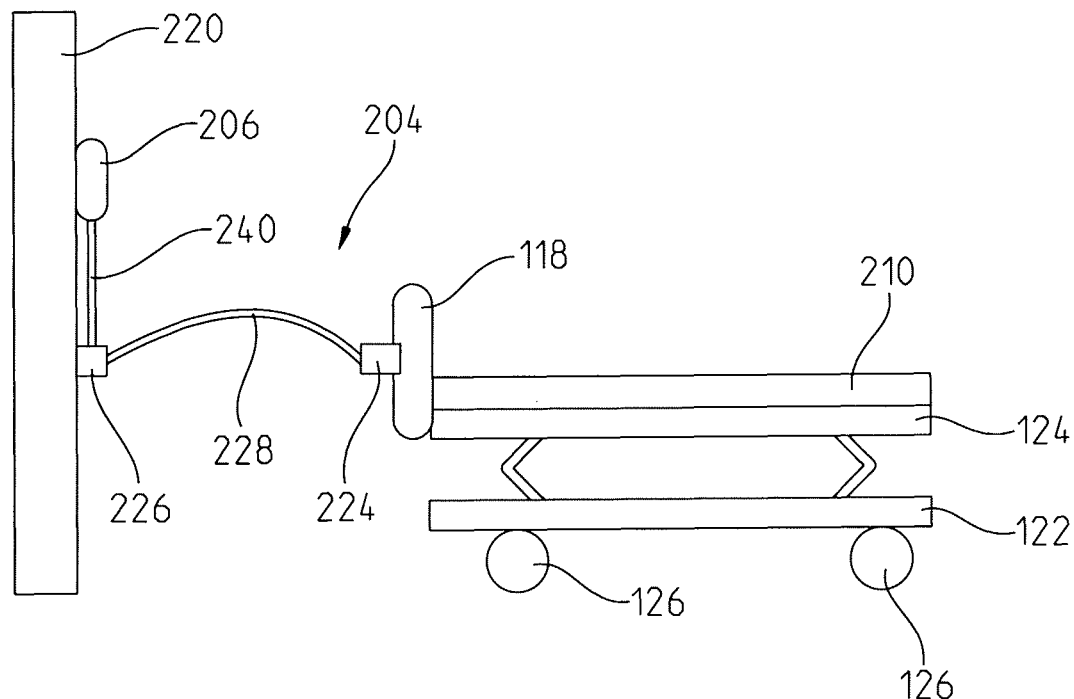
Figure 5D:
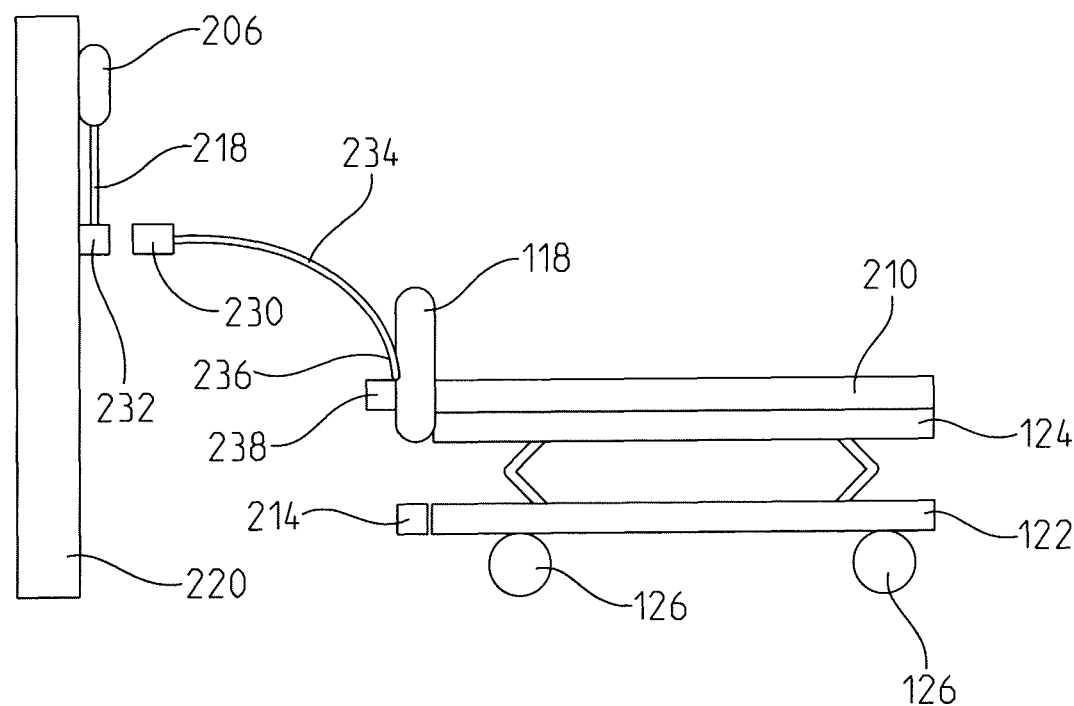

FIGS. 5A, 5B, and 5D illustrate three possible implementations of an infrared-based communications link between a non-bed mounted user interface 206 and a bed 210, while FIG. 5C illustrates one possible implementation of a fiber-optic based communications link between a non-bed mounted user interface 206 and a bed 210.

As discussed above, the bed 210 generally has a headboard 118, a deck 124, which supports a mattress, a frame 122, and a number of wheels. In the illustrated configurations, the head end of the bed 210 is positioned adjacent a wall or other support structure 220 (such as a headwall, support column, table or cart), which supports the non-bed mounted user interface 206. While the drawings show the non-bed mounted user interface 206 generally positioned above a headboard 118 of the bed 210, such arrangement of the non-bed mounted user interface 206 relative to the bed 210 is not required. The non-bed mounted user interface 206 may be located anywhere in the room (e.g. away from the bed or beds 210 or another more convenient location for access by a caregiver or staff member), with the only limiting factor being the length of the transmission cable. Fiber optic cables in particular can communicate over long distances (e.g. 20 meters or longer), and are thus suitable if it is desirable to locate the non-bed mounted user interface 206 farther away from the bed 210.

In FIG. 5A, the communication link 204 includes wired and wireless components. Wireless communication occurs from the bed 210 to the floor, and wired communication occurs from the floor to the non-bed mounted user interface 206. A wireless infrared transceiver 214 is attached to the bed frame 122 (e.g. mounted to a panel of the bed frame 122). In the drawing, the wireless infrared transceiver 214 is attached to a bottom surface of the bed frame 122, although any suitable location on the bed 210 may be used. A serial cable (not shown) connects the bed transceiver 214 to a bridge board of the bed communication interface 202.

Another wireless infrared transceiver 216 is spaced from the wireless infrared transceiver 214 but is in the line-of-sight of the wireless infrared transceiver 214. In the drawing, the wireless infrared transceiver 216 is supported by a bed docking unit 212. The bed docking unit has an internal channel that is sized to receive one of the wheels 126. Insertion of the wheel 126 into the bed docking unit 212 facilitates alignment of the transceivers 214, 216. One suitable bed docking unit 212 is a modified version of the P958 bed locator available from the Hill-Rom Company, Inc. The P958 bed locator is modified to attach the transceiver 216 thereto. The transceiver 216 is connected to a cable 218, which connects to a serial port (e.g. RS-232 or USB) of the non-bed mounted user interface 206.

FIG. 5B illustrates a configuration that is similar to that shown in FIG. 5A, except that the transceiver 216 is mounted to the structure 220 rather than to the bed docking unit 221, so that wireless transmission occurs horizontally (i.e. between the bed 210 and the structure 220) rather than vertically (i.e. between the bed 210 and a floor-based transceiver).

FIG. 5D illustrates a configuration in which an infrared transceiver 230 is mounted to one end of a cable assembly 234. The other end 236 of the cable 234 (nearest the bed 210) has an infrared transceiver 238 attached thereto that is aligned with an infrared transceiver that is attached to the bed frame 122 (e.g. transceiver 214).

Alignment of the infrared transceivers 238, 214 at the bed 210 is achieved by attaching the transceiver 238 to the bed 210 at a suitable location for line-of-sight communication with the transceiver 214, using a non-permanent fastener such as a hook and loop fastener (e.g. Velcro®), magnets, or other suitable fastener. The transceiver 230 is aligned with a transceiver 232 in a similar non-permanent fashion. For example, the transceiver 230 may be attached to the support 220 via a hook and loop fastener, magnet or other suitable fastener, or the transceiver 230 may simply be supported by the floor in a line-of-sight with the transceiver 232.

The non-permanent positioning of the transceivers 238, 230 allows one or more of the transceivers 230, 238 to disengage without damaging any of the transceivers 214, 238, 230, 232 or the cables 218, 234, if the bed 210 is moved prior to being disconnected from the non-bed mounted user interface 206.

The transceivers 232, 230, and 238, and the lengths of the cables 218, 234, may be configured to achieve any suitable arrangement, e.g. so that the cable 234 runs along the floor or so that the cable 234 is secured above the floor (e.g. by a clip or other fastener mounted to the structure 220).

Wireless communication occurs between the two infrared transceivers 214, 238 located at the bed 210 and between the transceiver 230 and the transceiver 232. The transceiver 232 is connected to the cable 218, which is connected to a serial port (e.g. RS232 or USB) of the non-bed mounted user interface 206.

FIG. 5C illustrates a configuration that uses fiber optic communications. In general, the fiber optic communications use a glass or plastic fiber 228, and connectors and transceivers shown schematically as elements 224, 226. The fiber optic cable 228 is used in place of an electric cable. The fiber optic transceiver 224 connects via a cable (not shown) to a serial port (e.g. RS-232 or USB) of a bridge board of the communication interface 202. The fiber optic transceiver 226 connects to the cable 240, which connects to a serial port of the non-bed mounted user interface 206.

Another alternative configuration involving wireless communication is schematically similar to the configuration shown in FIG. 5C, except that a low power wireless network or wireless personal area network (WPAN) is used in place of fiber optic or infrared communications. In order to illustrate the low power wireless or WPAN configuration, the cable 228 would be eliminated from the FIG. 5C schematic and wireless data transceivers would be used in place of the fiber optic transceivers.

The low power wireless or WPAN networks typically have a limited communication range in comparison to other wireless networks (such as an 802.11 wireless LAN). As such, the low power wireless network or WPAN can be configured to detect beds or devices in the patient room 12 and/or adjacent rooms rather than all of the beds on the same floor.

In a low power wireless or WPAN configuration, a wireless communication protocol is used that has a limited communication distance. Some examples of suitable protocols include Zigbee, Bluetooth, SimpliciTI and ANT. Computer-executable instructions resident in the non-bed mounted user interface 206 and/or the bed controller 192 is configured to search for compatible wireless devices in the communication area and to ignore incompatible devices. The computer-executable instructions may be configured to ignore devices that are not located in the patient room 12 or in a specified area surrounding the patient room 12.

However, in some cases, it may be desirable to allow certain devices in adjacent rooms to connect to the network of the patient room 12, so that status information from the adjacent room can be displayed at the non-bed mounted user interface 206. For example, if a patient in an adjacent room is at risk for having an adverse event, it may be desirable for data from the bed (or another device) located in the adjacent room to be displayed to a caregiver located in the patient room 12 via the non-bed mounted user interface 206, so that the caregiver (who may be closest to the patient) can attend to the patient in a timely fashion if the patient experiences an adverse event.

If adjacent rooms are permitted to connect to the room's wireless network, the computer executable instructions can be configured to limit the features of the non-bed mounted user interface 206 that are available for devices in the adjacent room. For example, the non-bed mounted user interface 206 may display status information for the adjacent room, but not allow remote control of devices located in the adjacent room.

In a low power wireless or WPAN configuration, the non-bed mounted user interface 206 includes additional displays and user controls configured to allow a user to add the bed 210 (or other beds or devices) to the wireless network. Once a bed or other device is added to the network, the connection information for the bed or device is stored in nonvolatile memory at the non-bed mounted user interface 206 and/or the bed controller 192, so that if the connection is lost, it can be restored without requiring user intervention.

Once a connection is established between the non-bed mounted user interface 206 and the bed network 190 via a low power wireless network or WPAN, a network bridge including the requisite hardware and/or software and/or firmware as described above, facilitates the communications between the non-bed mounted user interface 206 and the bed controller 192.

Some examples of data and/or commands that can be sent to or from the bed to the non-bed mounted user interface 206 via communication signals using one of the communication methods described above include, but are not limited to: patient position monitoring/alarm mode, head of bed angle monitoring/alarm mode, pause alarm command, cancel alarm command, nurse call command, answer nurse call command, weigh scale command, patient weight, view patient history, patient environment information, communication type (e.g. broadcast, polled or event-based), patient position monitoring mode (e.g. out of bed, exiting bed, on edge of bed), audible alarm mode, mattress or surface mode (e.g. sleep, maxinflate, comfort adjust, pressure relief, heel relief, percussion, vibration, rotation, turn assist, alternating pressure, sleep mode, seat inflate, seat deflate), zero scale command, weigh patient command, indicator status (e.g. on, off, flashing, flashing slow, flashing fast, green, amber), bed cleaned indicator, head of bed angle indicator (e.g. below 30 degrees, below 45 degrees), turn reminder, room lights command or status, reading lights command or status, music control, television control, entertainment channel control, speaker volume control, CPR mode control, bed up/down control, bed high/low control, head up/down control, knee up/down control, foot up/down control, foot extend/retract control, bed flat (all deck sections at zero degrees), bed tilt (deck at 20 degrees reverse Trend), 15 degrees Trend, 15 degrees reverse Trend, chair position (head up 65 degrees, knee up 10 degrees, foot down 70 degrees), chair egress position (head up 75 degrees, knee at 0 degrees, foot down 85 degrees, foot in retracted position), recliner position (head up 50 degrees, knee up 10 degrees, foot lowered 30 degrees), configure NaviCare® alerts, activate or cancel NaviCare® alerts (where "NaviCare® alerts" refers to a system available from the Hill-Rom Company, Inc., that allows bed and surface data to be communicated to caregivers using the healthcare facility's communication network), among others.

The system 10 includes patient room and bed management features. FIGS. 6, 7A-7C, 8A, and 9 illustrate steps that may be implemented as executable computer instructions to provide patient room and bed management features of the system 10. The executable computer instructions may be implemented at the server 18 or at another computing device or devices of the system 10. In some versions, a non-bed mounted user interface 206 is used to implement one or more of the described features.

Figure 6:
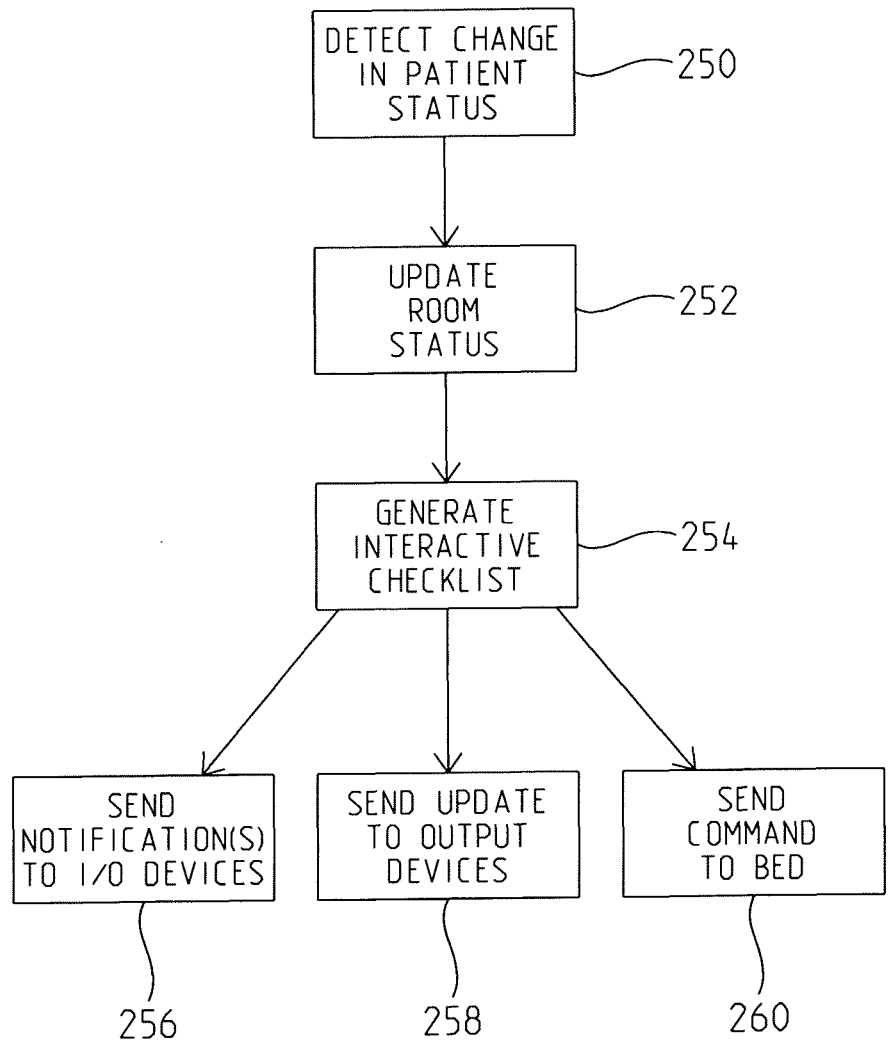
FIG. 6 is a flow diagram illustrating steps that are executable by a computer system to implement functions of a patient room and bed management system.

FIG. 6 illustrates a process by which the system 10 performs certain functions in response to a change in the status of a patient. At step 250, the system 10 determines that a patient's status has changed. In one version, the system 10 receives an indication of the patient's status from the HIS system 50. The patient's status may be manually input at the HIS system 50 by an authorized staff person, or may be determined systematically through the execution of computer-executable instructions. Alternatively or in addition, the system 10 may receive indications of patient status from other sources. For example, a caregiver or other authorized staff person may manually enter the patient's status at a master station 26, a patient station 34, 36, a non-bed mounted user interface 150, 152, 166, or a mobile device 90.

In any case, the patient status information received by the system 10 includes a patient identifier and a status identifier. Both the patient identifier and the status identifier are predefined as being associated with a particular patient and a particular status, respectively. Typically, identifiers such as these comprise alphabetical, numeric or alphanumeric codes. For example, a patient identifier may be a portion of a patient's driver's license number or Social Security number. A status identifier may be "A01" if the patient has been admitted to the facility, "A02" if the patient has been transferred to a new location in the facility, or "A03" if the patient has been discharged from the facility.

The illustrated version of the system 10 uses status identifiers associated with the admission, transfer and discharge of the patient, however, some versions of the system 10 are configurable so that other status identifiers may be specified alternatively or in addition to the admission, discharge and transfer status identifiers. For example, "interim" status identifiers may be defined, and may include, but are not limited to indications that: a patient is in transit (either to room from another location or vice versa), has had vital signs checked, has had initial consultation, is in surgery, is using the commode or shower, has received medications or therapy, and/or has received final instructions (e.g. for discharge). Each time the system 10 receives a status identifier for a patient, computer-executable instructions are executed to compare the value of the most recently received status identifier to the value of the previous status identifier received. If the new status identifier is different than the most recent previously-received status identifier, then the system 10 proceeds to step 252.

In addition to patient identifiers and patient status identifiers, the system 10 also receives, stores, and monitors patient room identifiers and room status identifiers. A patient room identifier identifies a particular room in the healthcare facility that has been assigned to a particular patient and a room status identifier indicates the current status of the patient's room. Typically, identifiers such as these comprise alphabetical, numeric or alphanumeric codes. A room identifier may be the room's unique room number in the healthcare facility (e.g., 101, 102, 200, 201, etc.). In some cases, the first digit of the room number may indicate the floor, wing, or unit of the healthcare facility in which the room is located while the remaining portion of the room number may identify the particular room on that floor, wing or unit. If the room is not a private room, the room identifier may also include a bed location identifier to identify which of the beds in the patient room is assigned to the patient. A bed location identifier may be appended to the end of the room identifier. For example, room identifiers "101-A," "101-B" include a bed location identifier, where "A" and "B" designate different bed locations in Room 101 (e.g. "A" may refer to the bed that is closest to the door while "B" may refer to the bed that is closest to the window). For implementations of the system 10 in non-private rooms, references herein to a "room" or "room status" generally refer not only to a room but also a particular bed in the room.

The bed location identifier may be an alphanumeric character that is only unique when combined with the room number, as shown in the foregoing example, or may include a unique serial number or other data that is associated with a particular bed (which may be referred to as a "bed identifier"). In one version of the system 10, a bed's specific data (such as serial number, make, model, configuration) is associated with the bed location identifier (e.g. 101-A) by a database, lookup table or similar computer programming device, once a particular bed is connected to the system 10 at a particular bed location, using one of the bed connectivity mechanisms described above.

Each room in the healthcare facility (or room-bed combination, as the case may be) is assigned a status by the system 10, which is stored in memory. Some examples of room status identifiers include, but are not limited to "room not ready" or "room dirty," "room clean," "room ready," "room occupied," "bed scale zeroed," and "bed scale not zeroed."

In one version of the system 10, the "room not ready" or "room dirty" room status is triggered by an indication that the patient has been discharged from the facility or transferred from the room to another location in the facility. The "room clean" room status is triggered by an indication that the room has been cleaned, but a bed associated with the room may not have been zeroed, and/or final preparations for a new patient may not have been completed.

The "room ready" room status is triggered by manual input from an authorized user. Before the system 10 will change the room status to "room ready," the system 10 will perform a series of checks to make sure that all of the requirements for declaring a room ready for a new patient have been completed, as described below. In general, a status of "room ready" means that the room has been cleaned, the bed-integrated scale has been zeroed, and final preparations have been completed. For rooms that have a status of "room ready," the room status may be updated to "occupied" once a patient has been admitted and assigned to the room.

The "bed scale zeroed" and "bed scale not zeroed" status indicators may be used in addition to the room status indicators described above. For example, a room may have a status of "room clean/bed scale not zeroed," or "room not ready/bed scale zeroed."

In general, aspects of the identifiers described above may be pre-specified or configured during system installation, according to the requirements of a particular healthcare facility.

The computer-executable instructions of the system 10 generally include Boolean-style logic statements that when executed, determine whether one or more of multiple possible actions are to be taken. At step 252, the system 10 executes Boolean-style logic to determine, based on the patient's status, whether the status of the patient's room is to be changed. The Boolean-style logic may be pre-specified or configured to implement business rules of a particular healthcare facility (which rules may incorporate Joint Commission on the Accreditation of Health Organizations or JCAHO requirements and/or other standards, regulations or guidelines that need to be observed for compliance and/or accreditation). In one version of the system 10, the status of a patient's room is changed to "dirty" or "needs cleaning" if the patient's status is determined to be "discharged" or "transported-out of room." If the patient's status is "admitted" (and not "transport") then the status of the patient's room is "occupied."

While not specifically shown in FIG. 6, the determination of whether to update the room status (step 252) may be triggered by factors other than a change in the patient's status. For example, if the system 10 receives a communication from a staff person associated with the housekeeping unit, indicating that the room cleaning has been completed, the room status may be updated to "room cleaned."

If the system 10 determines that a change in status of the patient's room is warranted, then the room status is updated in the memory and the system 10 proceeds to step 254. At step 254, the system 10 executes Boolean-style logic to determine whether the change in room status should trigger the creation of an interactive checklist of actions to be performed by a caregiver or other staff person associated with the healthcare facility. The determination of whether to generate a checklist, as well as the particular action items to include in the checklist, may be pre-specified or configured to implement business rules of a particular healthcare facility. If the system 10 determines that the change in room status does not trigger the generation of a checklist, then the system 10 skips the remainder of step 254 and proceeds to one or more of steps 256, 258 and 260.

If the system determines that the change in status of the patient's room warrants the creation of a checklist, then the system 10 determines the action items to include in the checklist and displays the checklist on a user interface located in the patient's room (e.g., on a non-bed mounted user interface 206, an on-board bed user interface 198, or a patient station 34, 36).

Action items included in the checklist may be actions that are performed by caregivers, housekeeping staff, or other staff persons associated with the facility. Some examples of action items that may be included in the checklist include, but are not limited to: clean the room, zero the scale, weigh the patient, provide fresh water jug, provide full box of tissues, place sheets on the bed, clear the room exit of obstructions, take patient's temperature, provide new pillow for patient, provide blanket, check siderails up, check bed brake set, check bed in low position, check bed patient position monitor (e.g. armed or not armed), provide red footies to falls risk patient, final room check complete, and/or nursing round complete.

Alternatively or in addition, the action items may be grouped by staff member type. For example, one checklist may be provided for caregivers and a different checklist may be provided for housekeeping staff; or a single checklist may be provided with action items grouped therein by the type of staff member. The staff member type may be obtained by the system 10 from wireless (e.g. infrared) signals transmitted from the staff member's locating and tracking badge to a wireless (e.g. infrared) receiver located in the patient's room (e.g. on a patient station 34, 36 or a non-bed mounted user interface 206). Upon determining the staff member type, the system 10 may generate the appropriate checklist.

In some versions of the checklist, the "clean the room" action item has a series of steps associated with it that comprise a sub-checklist. Some of the steps that may be included in a "clean the room" sub-checklist may include, but are not limited to: sanitize the lavatory, clean the floor, sanitize the bed, replace the bed sheets, adjust the room temperature control, and/or confirm that the room is clean.

Some versions of the checklist include a series of action items that are typically performed by a caregiver in connection with the discharge of a patient. These action items may include, but are not limited to: explain departure process to patient, provide training materials or instructions to patient, review prescriptions, medications and/or therapies with patient, notify patient's family, notify transport department, and/or mark the patient's room as dirty.

Similarly, some versions of the checklist may include additional or alternative action items that may relate to the admission or transfer of a patient. Some additional or alternative items that may be included in a checklist include, but are not limited to: escort patient to room, meet patient in room, verify patient's identity (e.g. vs. wristband), verify procedure(s) scheduled for patient, schedule physician visit, provide patient garments (e.g. gown, footies), wash hands, and/or request wheelchair.

The checklist is interactive in that it includes user controls that allow a user to "check off" action items at the in-room user interface (206, 198, 34, 36) as they are completed. In the illustrated version of the system 10, the interactive checklist is implemented as a touchscreen user interface, although a non-touchscreen user interface and hardpanel controls may also be used. One example of an interactive checklist is shown in FIGS. 11A-11D, described below.

Once a user has indicated at an in-room user interface (e.g. 206, 198, 34, 36) that a particular action item has been completed, the system 10 updates the checklist on the in-room user interface(s). The system 10 may also send a signal to the server 18 and/or the HIS system 50 indicating that the action item has been confirmed as completed by the user.

The server 18 and/or the HIS system 50 may use the action item completion information to trigger other actions. For example, if a housekeeping staff person indicates that room cleaning is complete, the server 18 may send a notification to a caregiver to let the caregiver know that the room is ready for final preparations for a new patient. As another example, if a caregiver indicates that the room is ready for a new patient, the HIS system 50 may mark the room as "available" and prompt a user of the HIS system 50 to assign a newly admitted or transferred patient to the room, or the HIS system 50 may assign the newly admitted or transferred patient to the room automatically without user intervention. Any automatic room assignments may be subject to confirmation by a user.

If a change in room status has occurred, then the system 10 may proceed to step 256 alternatively or in addition to step 254. At step 256, the system 10 sends a notification to an input/output device that is connected to the system 10 using the communication links described above. For example, if the room status has changed to "dirty," then the system 10 sends a message to an input/output device associated with a staff person (such as a mobile device 90, or a patient station 34, 36) associated with the housekeeping unit to let them know that the room is ready to be cleaned. If the room status has changed to "clean," then the system 10 sends a message to an input/output device associated with a caregiver (such as a mobile device 90, a master station 26, or a patient station 34, 36) to let them know that the room is ready for final preparation tasks to be performed to ready the room for a new patient.

If a change in room status has occurred, then the system 10 may, alternatively or in addition to step 256, proceed to step 258. At step 258, the system 10 sends an update of the room status to one or more output devices that are connected to the system 10, using the communication links described above. For example, an electronic status board 30 may be updated to reflect the new status of the room. Also (particularly if the room status has changed to "dirty," the system 10 may issue a command or control signal to the indicator assembly 32 associated with the room to activate one of its light panels and/or to generate an audible tone, e.g. to catch the attention of staff persons in the area who are responsible for attending to the room.

If a change in room status has occurred, then the system 10 may, alternatively or in addition to step 256, and/or step 258, proceed to step 260. At step 260, the system 10 determines (e.g. using Boolean-style logic implementing business rules of the healthcare facility) whether an electronically-controlled function needs to be performed at the bed associated with the patient (in the patient's room) in response to the change in room status.

In one version of the system 10, if a bed function needs to be performed, then the system 10 sends a command or control signal directly to the associated bed (which is identified to the system 10 using the patient, room and bed identifiers described above). The bed controller 192 receives the command or control signal via the bed network 190 and the communication links described above. The bed controller 192 interprets the command or control signal and issues the appropriate signals to the appropriate bed function control modules and/or electromechanical components of the bed, to execute the bed function. As one example, if the system 10 determines that the room has been cleaned and final preparations have been completed, but the bed's weigh scale has not been zeroed, then the system 10 will issue a command directly to the bed controller 192 to initiate zeroing of the weigh scale (e.g. automatically, without user intervention).

In another version of the system 10, in response to a change in room status, the system 10 sends a signal to one or more input/output devices located in the bed's room (such as a non-bed mounted user interface 206, a bed-mounted user interface 198, and/or a patient station 34, 36) indicating that a particular bed function needs to be performed. The system 10 then waits for user input at one of these in-room input/output devices (e.g. the user touches a "zero scale" touchscreen control button) before commanding the bed controller 192 to perform the specified function.

When the bed function has been performed, the bed controller 192 may send a signal to the system 10 indicating that the function has been completed. Upon receipt of such a signal from the bed controller 192, the system 10 may send a notification to one or more input/output devices, send an update to an output device, or initiate some other activity within the system 10. For example, if the bed's weigh scale has been successfully zeroed, the system 10 may update the status of the room to "scale zeroed," at which point the change in status of the room may trigger another event or series of events stemming from step 252 of FIG. 6 as described above.

Once a patient room has been assigned a status of "ready" (indicating that all preparatory actions have been completed), the system 10 may send a notification to the HIS system 50 (or to mobile or non-mobile input/output devices of staff persons associated with the HIS system 50) to indicate that the room is ready and available to receive a new patient.

Zeroing the bed's weigh scale is one example of a bed function that can be remotely initiated by the system 10 based on room and/or patient status. Other bed functions that may be controlled in a similar fashion include, but are not limited to: clearing patient position monitoring settings, turning off patient position alerts (e.g. bed exit alarm), turning off head of bed angle alerts, clearing patient history data (such as patient weight and/or therapy histories), controlling bed indicator lights (e.g. SafeView lights), and controlling room lights, controlling reading lights.

Figure 7A:
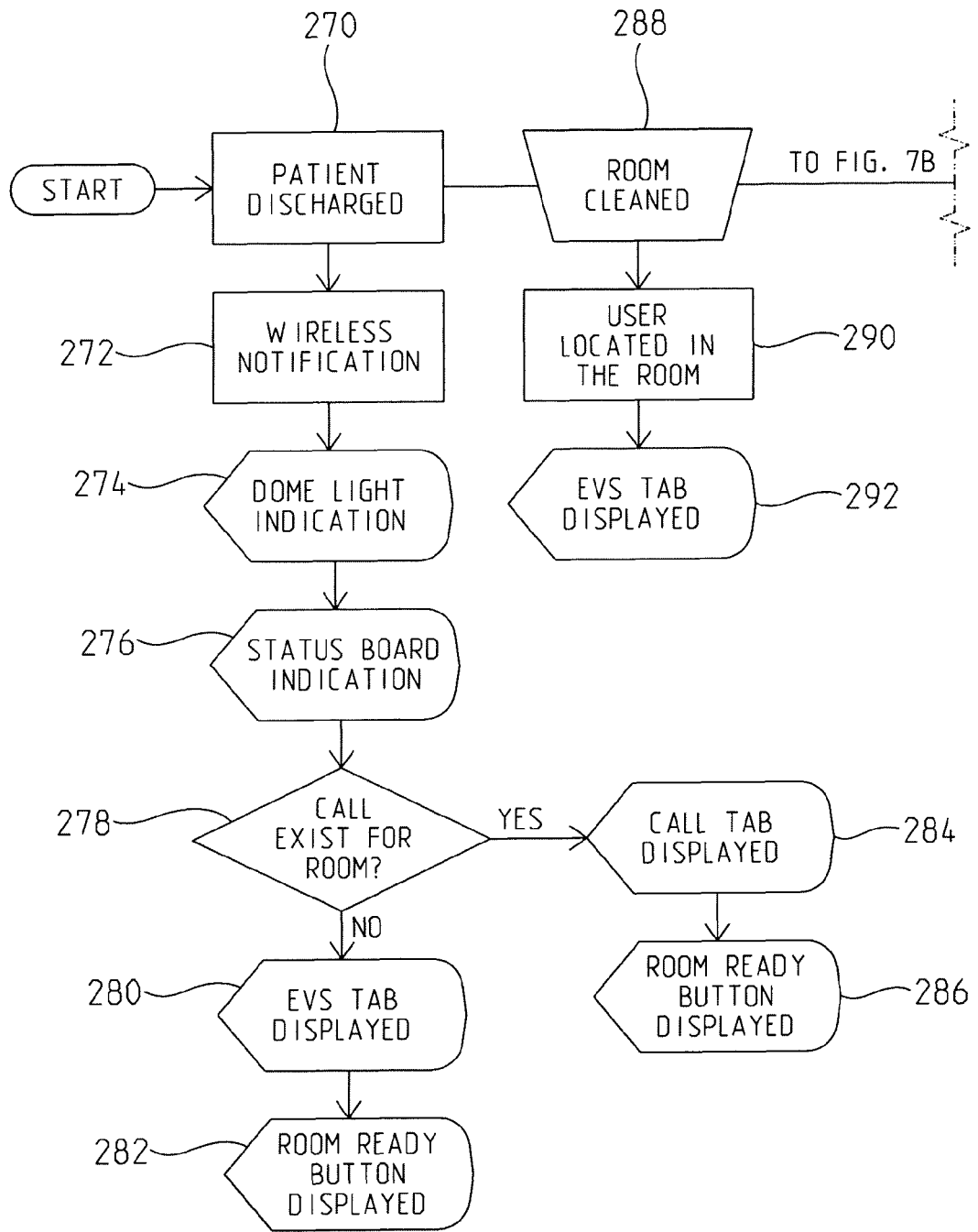
FIGS. 7A-7C are flow diagrams illustrating another version of steps that are executable by a computer system to implement functions of a patient room and bed management system.
Figure 7B:
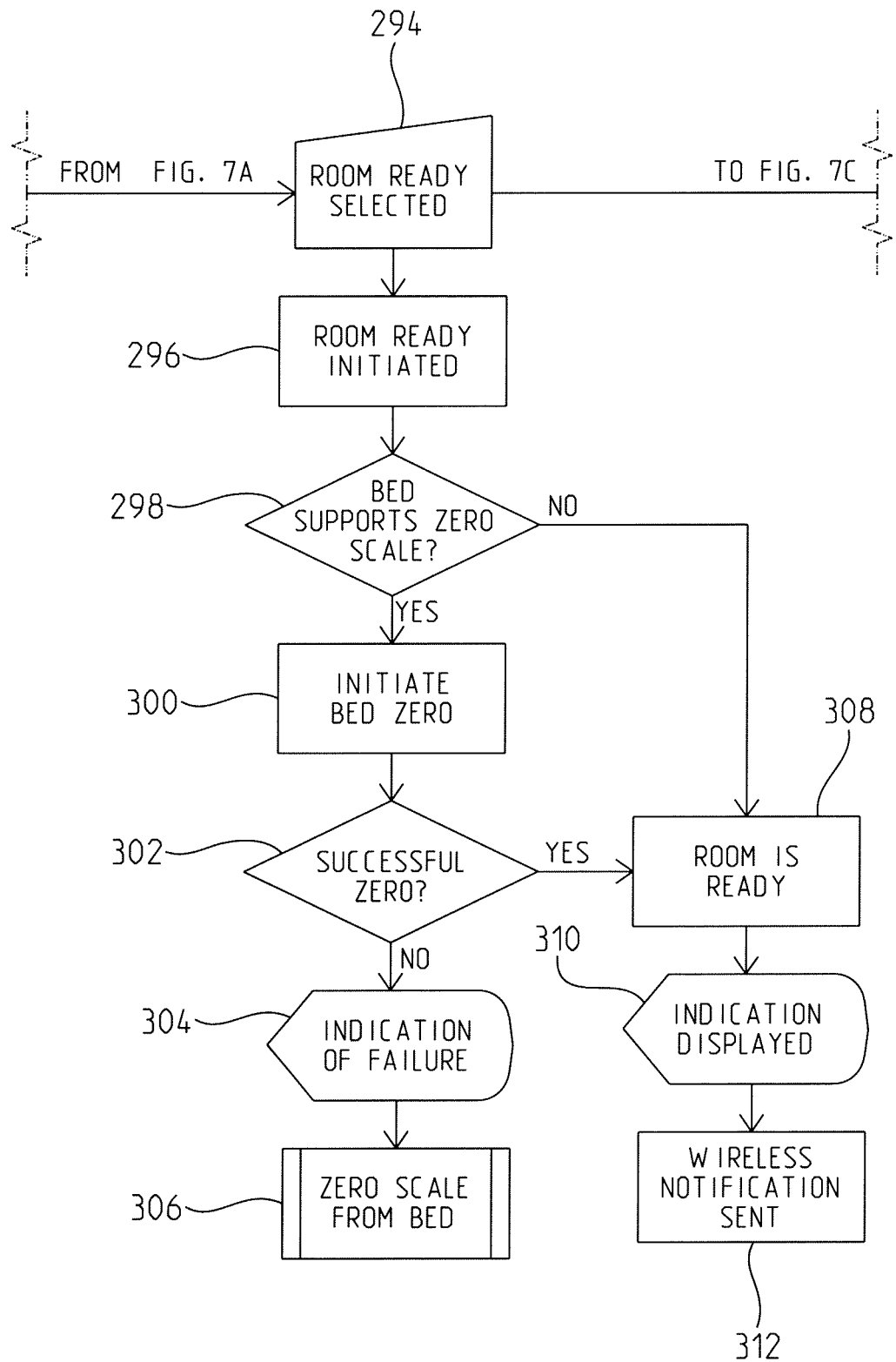
Figure 7C:
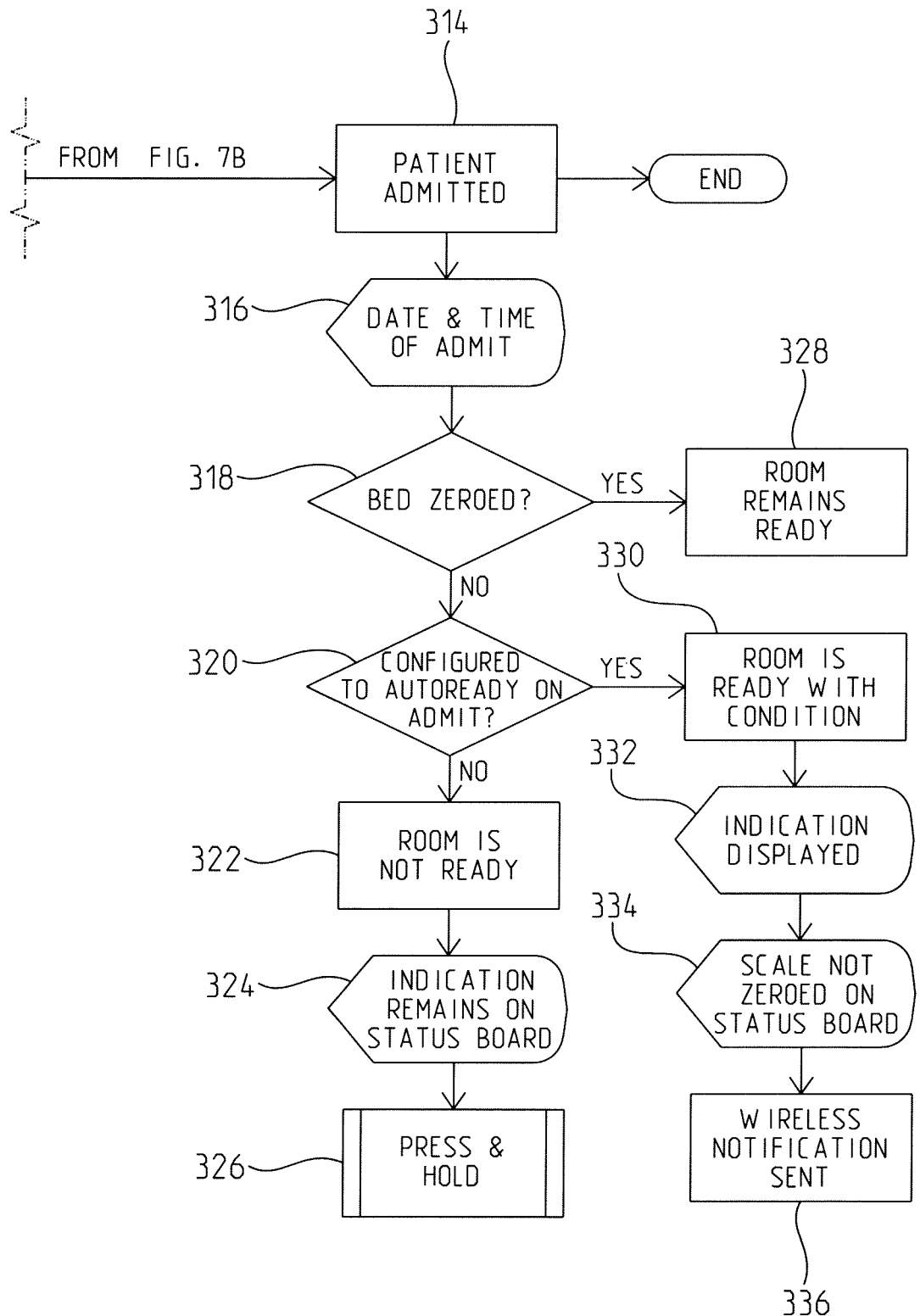

FIGS. 7A-7C illustrate a version of steps that may be implemented as executable computer instructions to provide an automated room ready process. The room ready process of FIGS. 7A-7C is initiated upon receipt by the system 10 of an indication that a particular patient has been discharged from the healthcare facility, as indicated at step 270. The patient discharge information (which includes a patient identifier and a discharge indicator) may be transmitted to the system 10 by the HIS system 50 using the communication links described above or may be manually input at a user interface. At step 272, a notification that the patient has been discharged is transmitted wirelessly to one or more remote communication devices (such as mobile units 80).

At step 274, the indicator assembly (e.g. "dome light") associated with the patient's room is illuminated to display an indication that the room needs cleaning or is not ready. The patient's room is identified using the patient identifier and a room identifier as described above. If the room includes multiple patient beds, the patient's bed is identified using the patient identifier, the room identifier, and the bed identifier or bed location identifier as described above.

At step 276, the new room status (e.g. needs cleaning or not ready) is displayed on an electronic status board 30. Also, at the in-room non-bed mounted user interface(s) (34, 36, and/or 206), a "room ready" user control on the user interface is made available to be selected.

Figure 14:
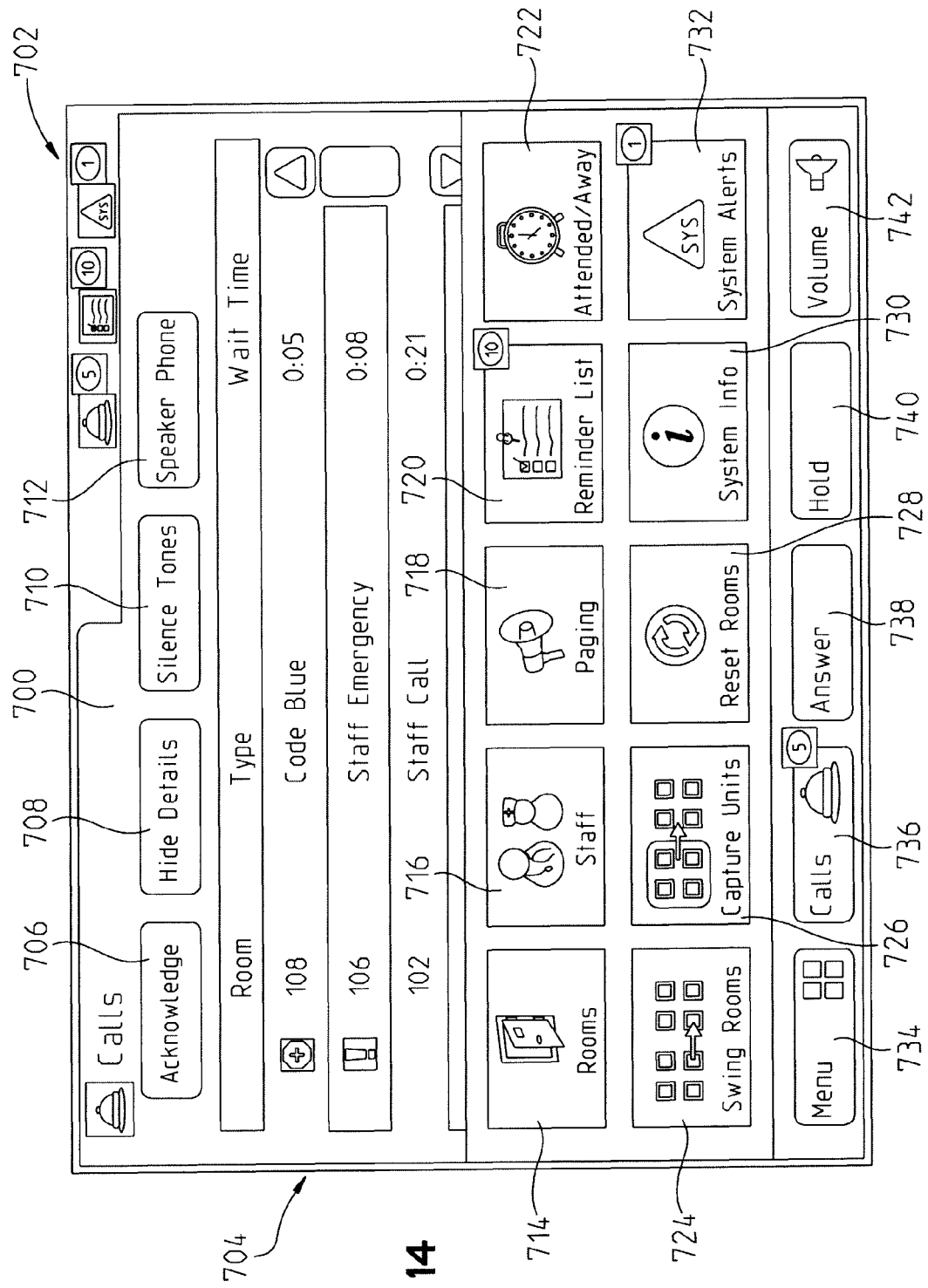

At step 278, a determination is made as to whether any calls have been made from the room (e.g. a call to a staff person to conduct the room cleaning). If no calls have been made, or if the system 10 detects that a member of the housekeeping staff is located in the room (e.g. via receipt of a wireless signal from a locating and tracking tag), then at step 280, a display screen showing information and functions applicable to housekeeping staff (e.g. a checklist of action items associated with cleaning the room) is displayed at the in-room non-bed mounted user interface(s) (e.g. 34, 36, and/or 206). If a call is pending, then at step 284 a display screen showing the status of all pending calls is displayed. One example of a calls display screen is shown in FIG. 14. At step 286, a "room ready" user control on the in-room non-bed mounted user interface(s) (e.g. 34, 36, and/or 206) is made available to be selected.

Step 288 is a manual step performed by a staff person associated with the healthcare facility. At step 288, the room needing to be cleaned is cleaned by a staff person. At step 290, the system 10 verifies that the staff person is located in the room (e.g. via a locating and tracking tag and wireless receiver located at an in-room non-bed mounted user interface(s) (e.g. 34, 36, and/or 206).

At step 292, a display screen showing information and functions applicable to housekeeping staff (e.g. a checklist of action items to be performed during room cleaning) is displayed at the in-room non-bed mounted user interface(s) (e.g. 34, 36, and/or 206) and a "room ready" user control on the in-room non-bed mounted user interface(s) (e.g. 34, 36, and/or 206) is made available to be selected.

Referring to FIG. 7B, at step 294, the staff person selects the "room ready" control or otherwise initiates a signal to the system 10 that activates the automated room ready process. At step 296, the system 10 initiates a number of automated functions of the automated room ready process.

Some beds that may be connected to the system 10 may not have an integrated weigh scale, or may have a scale but the scale can only be zeroed from a bed-mounted user interface 198. At step 298, the system 10 determines whether the bed in the room associated with the patient supports remote bed scale zeroing. If the bed has an integrated bed scale that can be zeroed by the system 10, then zeroing of the bed scale is initiated at step 300 by sending a command or control signal to the bed controller 192 as discussed above. If the bed does not support remote bed scale zeroing, then the system 10 proceeds to step 308, discussed below.

At step 302, the system 10 checks to see if the bed scale zeroing step 300 was completed successfully. For example, the system 10 may wait for either a scale zeroed confirmation signal or an error signal to be received from the bed controller 192. If the bed scale was successfully zeroed, then the system 10 displays the date and time that the scale was zeroed at one or more of the user interfaces 34, 36, 206. FIGS. 10, 11C, 11D, and 11E illustrate user interface displays that include a scale zeroed date and time stamp.

Figure 8A:
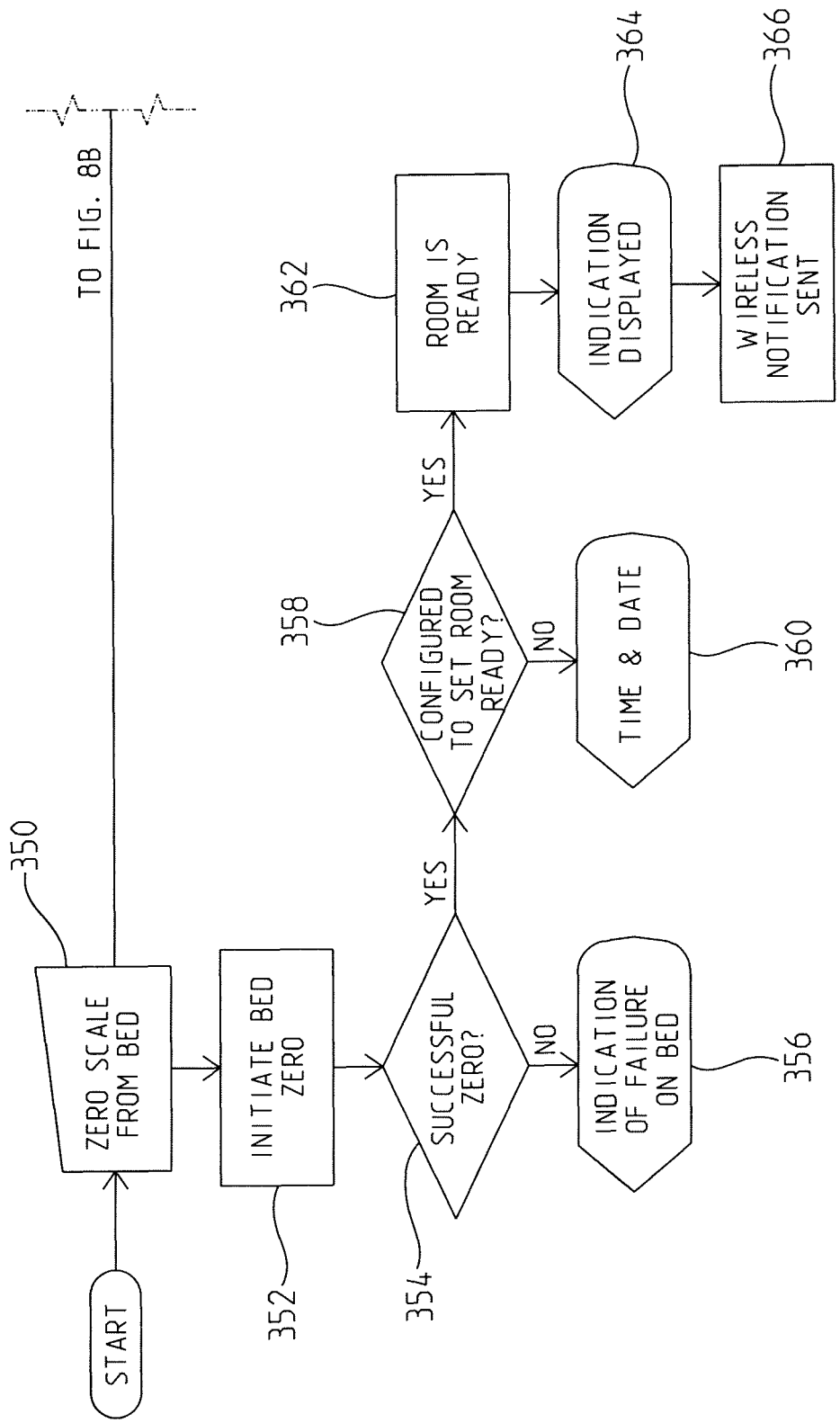
FIGS. 8A-8B are flow diagrams illustrating additional steps that are executable by a computer system to implement functions of a patient room and bed management system.
Figure 8B:
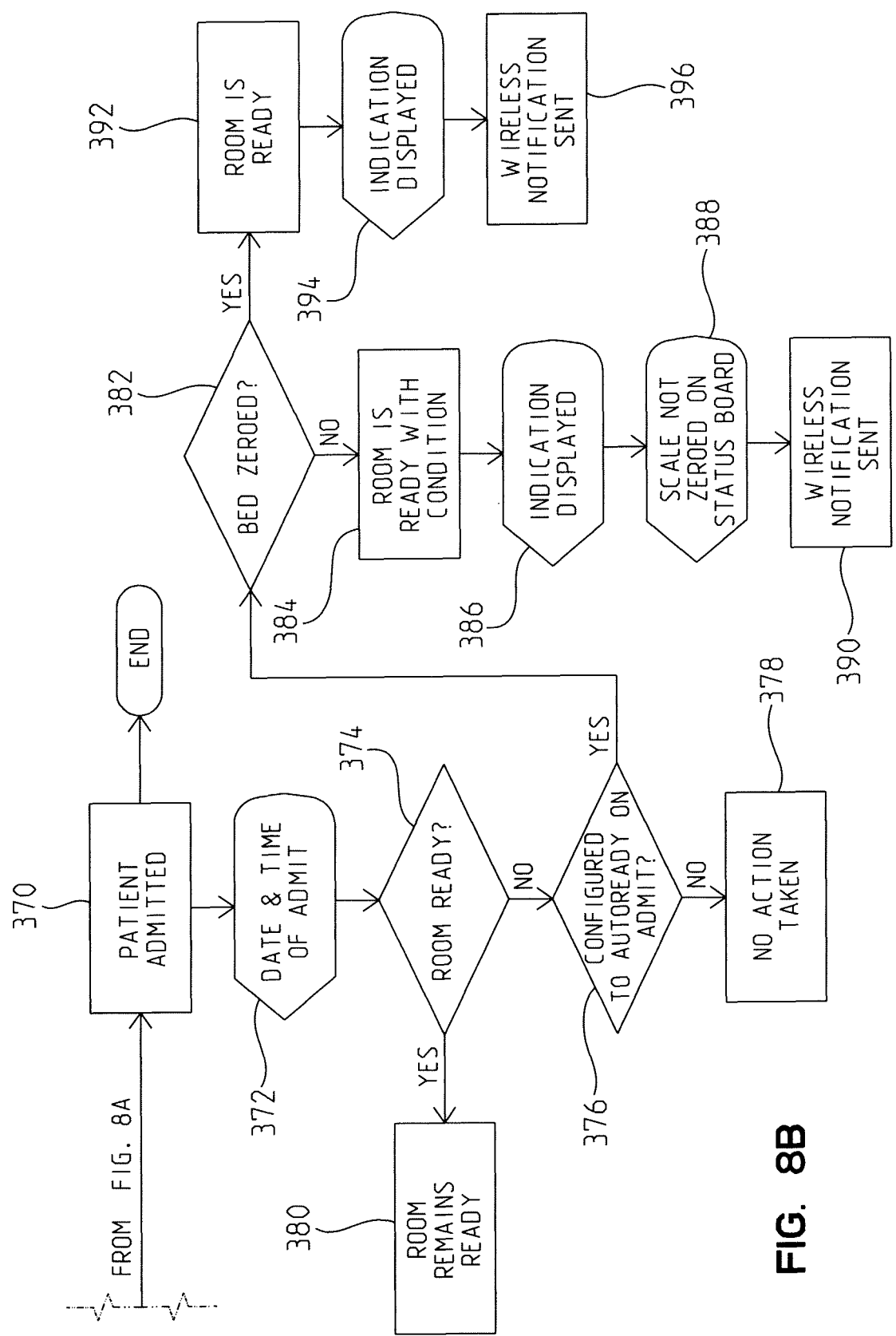

If the bed scale did not zero successfully, then at step 302 an indication is displayed at one or more of the user interfaces 34, 36, 206. Step 306 initiates a process of zeroing the bed scale from one of the on-board bed control modules 198 (e.g. 128, 130). A process for zeroing the bed scale from a bed-mounted user interface is illustrated in FIGS. 8A-8B, described below.

Referring to step 308, once the room has been verified as cleaned and the bed scale has been successfully zeroed (if the bed supports scale zeroing), then the system 10 updates the status of the room to "ready." When the room status has changed to "ready," the system 10 updates the status of the room to "ready" on the electronic status board 30 and removes or turns off the "room not ready" indication at the indicator assembly 32 associated with the room, at step 310. At step 312, the system 10 sends a wireless notification indicating that the room status is now "clean," to mobile devices of caregivers or other staff persons and/or other input/output devices according to the requirements of a particular configuration of the system 10, using the communication links described above.

Referring to FIG. 7C, the system 10 detects that a patient has been admitted to the healthcare facility at step 314. The patient admit information (which includes a patient identifier and an admit indicator) may be transmitted to the system 10 by the HIS system 50 using the communication links described above or may be manually input at a user interface. The business rules of a healthcare facility may require that an admitted patient only be assigned to a room that has a status of "ready."

The system 10 associates the patient with his or her assigned room and/or bed using the patient identifier, room identifier, and bed identifier or bed location identifier as described above. At step 316, the system 10 displays the date and time the patient was admitted to the facility and an identifier of the room assigned to the patient on one or more of the in-room non-bed mounted user interfaces 34, 36, 206 located in the room assigned to the patient.

At step 318, the system 10 determines whether the bed-integrated weigh scale has been zeroed before the patient has been admitted to the room by checking the date and time stamp of the last bed scale zeroing and comparing it to the date and time stamp of the patient admit. If the bed scale has been zeroed within the appropriate time frame, the room status remains as "ready" (step 328).

Figure 9:
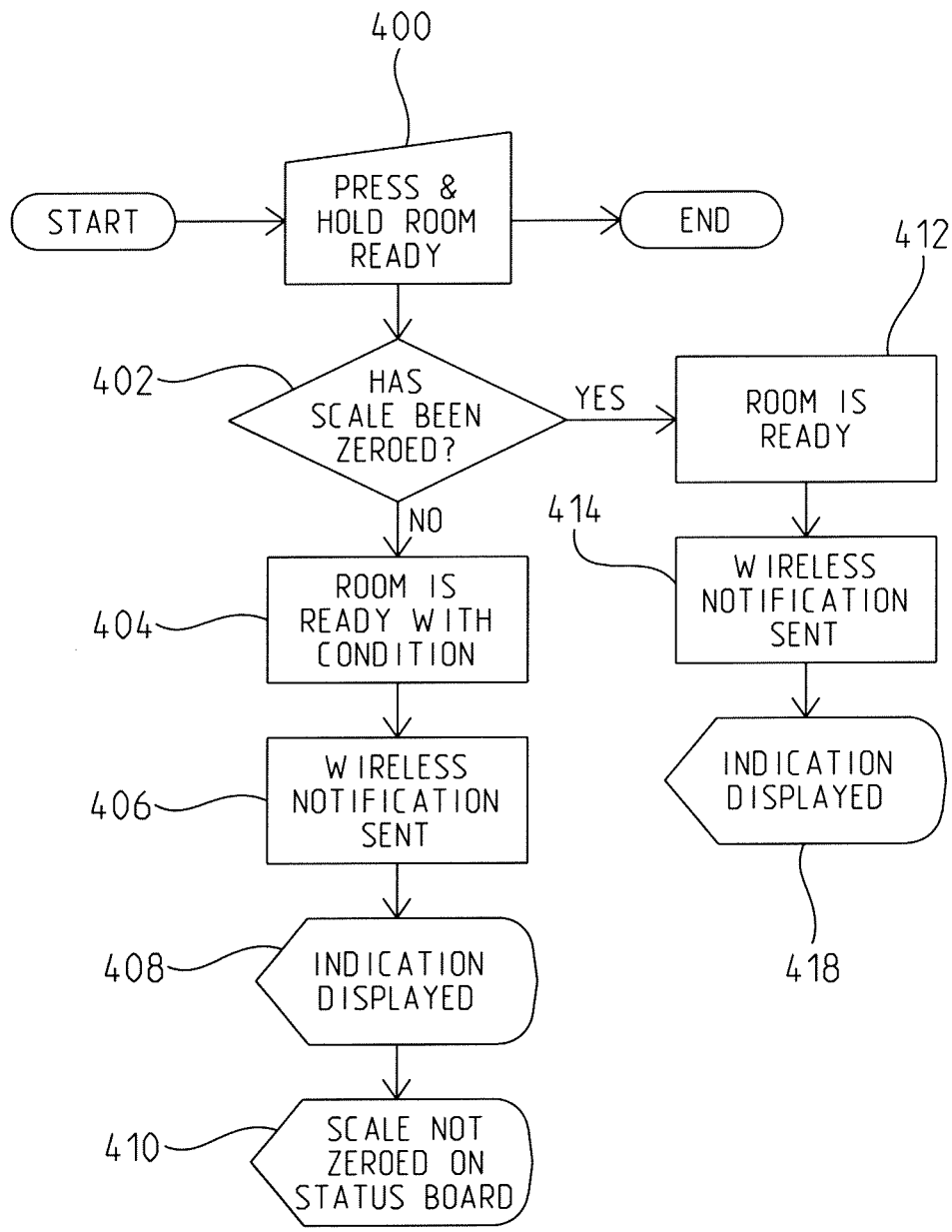
FIG. 9 is a flow diagram illustrating additional steps that are executable by a computer system to implement functions of a patient room and bed management system.

If the bed scale has not been zeroed within the appropriate time frame, then the system 10 checks to see if it has been configured to allow rooms to automatically be determined to be ready upon patient admit (step 320). If the system 10 has not been configured to allow the automatic room ready, then the room status is set to "not ready" (step 322). At step 324, the room status of "not ready" is displayed on the electronic status board 30 and/or one or more of the in-room user interfaces 34, 36, 206. Also, at step 326, a "press and hold" feature activated by pressing and holding the room ready button, is initiated. The press and hold feature is illustrated in FIG. 9.

If the system 10 has been configured to allow the automatic room ready, then at step 330 the room status is updated to "ready with condition," because the bed scale has not been zeroed within the requisite time period. An indication that the bed scale needs to be zeroed is displayed at the indicator assembly 32 and the electronic status board 30. A user control for zeroing the scale may be made available at one of the non-bed mounted user interfaces 34, 36, 206, and/or an indication that the bed scale has not been zeroed is displayed thereon (steps 332, 334). The system 10 sends wireless notifications that the bed scale needs to be zeroed, or simply that the room is ready with a condition, to mobile devices and/or other input/output devices as described above.

FIGS. 8A-8B illustrate steps that may be implemented as executable computer instructions to manage patient room and bed features, which may be triggered by the determination that the bed scale cannot be zeroed remotely through the system 10 but rather must be zeroed using an on-board bed user interface 198. At step 350, a user zeroes the bed scale from the on-board bed user interface 198 by activating a user control (e.g. a touch-sensitive button). At step 352, the bed controller 192 initiates zeroing of the bed scale.

At step 354, the system 10 determines (e.g. by detecting signals issued by the bed controller 192 over the bed network 190) whether the zeroing of the bed scale has been successfully completed. If the bed scale zeroing fails, an error message is displayed at the bed-mounted user interface 198 and no date and time stamp for bed scale zeroing is issued (step 356). If the bed scale zeroing completed successfully, then the system 10 determines whether the system 10 has been configured to automatically initiate the room ready processes upon completion of bed zeroing from the bed (step 358). If the system 10 has not been so configured, then the date and time stamp of the successful zeroing is displayed at one or more of the non-bed mounted user interfaces 34, 36, 206 and no further action is initiated (step 360).

If the system 10 has been configured to initiate the room ready processes automatically upon completion of bed zeroing from the bed, then, upon successful bed scale zeroing at the on-board user interface 198, the room status is updated to "ready" (step 362). Also, room ready indications are displayed at step 364, and wireless notifications are sent at step 366 as described above. The room ready indications include the data and time stamp of the bed scale zeroing, the zero scale button made available for selecting, the housekeeping tab or user interface being displayed (which may include a checklist), displaying the room status as "ready" at the electronic status board 30, and removing or canceling the display of the "room needs cleaning" indication at the indicator assembly 32 associated with the room.

Referring to FIG. 8B, continuing the process of zeroing the bed scale from the bed, a patient is admitted and the date and time stamp of the patient admit is recorded as described above in connection with steps 314, 316 of FIG. 7C (steps 370, 372). The system 10 then checks to see if the room status is "ready," and if so, no additional steps are taken (steps 374, 380). If the room status is not set to "ready," then the system executes step 376, which is similar to step 320 of FIG. 7C, described above. If the system 10 is not configured for automatic room ready on admit as described above, then no additional action is taken and the room status remains unchanged (step 378). If the system 10 is configured for automatic room ready on admit, then the system 10 determines whether the bed scale has been zeroed (step 382). If the bed scale has not been zeroed, then the system 10 executes the steps 384, 386, 388, 390, which are similar to the steps 330, 332, 334, 336 of FIG. 7C, described above.

If the bed scale has been zeroed, then the room status is updated to "ready" (step 392), room ready indications are displayed (step 394), and wireless notification(s) are sent (step 396) as described above. The room ready indications include the date and time stamp of the last successful bed zeroing, enabling of the zero scale user control on the user interface(s) 34, 36, 206), displaying the updated room status at the electronic status board 30, and removing the "room needs cleaning" indication at the indicator assembly 32.

FIG. 9 illustrates steps that may be implemented as executable computer instructions to manage bed and room features, which may be triggered by a user pressing and holding the "room ready" button on one of the user interfaces 34, 36, 206 at step 306 of FIG. 7B (also step 400 of FIG. 9). The "press and hold" feature allows a user to exert manual control to initiate the room ready process even if the system 10 indicates that the bed scale has not been zeroed or that the room status is not ready.

If the user presses and holds the room ready button, the system 10 determines if the bed scale has successfully been zeroed (step 402). If the bed scale has not been zeroed, then the system 10 executes steps 404, 406, 408, 410, which are similar to steps 384, 386, 388, 390 of FIG. 8B, described above. If the bed scale has been zeroed, then the system 10 executes steps 412, 414, 418, which are similar to steps 392, 394, 396 of FIG. 8B, described above.

FIG. 10 illustrates a room ready output display suitable for use on the non-bed mounted user interface 166. The display includes a zero scale control 434, which, when activated by a user, initiates zeroing of a bed-integrated weigh scale from the non-bed mounted user interface 166. The display also indicates, for each bed located in the room, whether the room-bed location (e.g. 101-A, 101-B) is ready to accept a new patient. A graphical indicator such as a check mark or graphical "x" is used to indicate the room status. The display also shows the date and time stamp for the last bed zeroing and the date and time stamps for the occurrences of the patient admit and patient discharge, as appropriate. The bed scale zeroing data is obtained from the patient's bed, and the patient status data is obtained from the HIS system 50 or manual input at a user interface. Alternatively or in addition to the zero scale control 434, the room ready display screen may include control buttons that initiate the execution of other bed functions. A non-exhaustive list of bed functions that may be remotely controlled at a non-bed mounted user interface is described above.

FIGS. 11A-11F illustrate a sequence of user interface screens suitable for use on one or more of the non-bed mounted user interfaces 150, 152, 166 to implement an interactive checklist feature of the room ready process.

The screen displays of FIGS. 11A-11F may be displayed when the housekeeping or "EVS" tab is selected, or when a member of the housekeeping staff is detected in the room as described above, or when the room status is "needs cleaning," as described above. The display includes a room identifier 440, a checklist 444, which includes a number of action items 446, 448, 450, and an indication of the current room status 442, 456, 462, 468, 472, 478, which changes as items on the checklist 444 are marked completed. The display also includes a user control 452 (e.g. a touch-sensitive button).

Figure 11A:
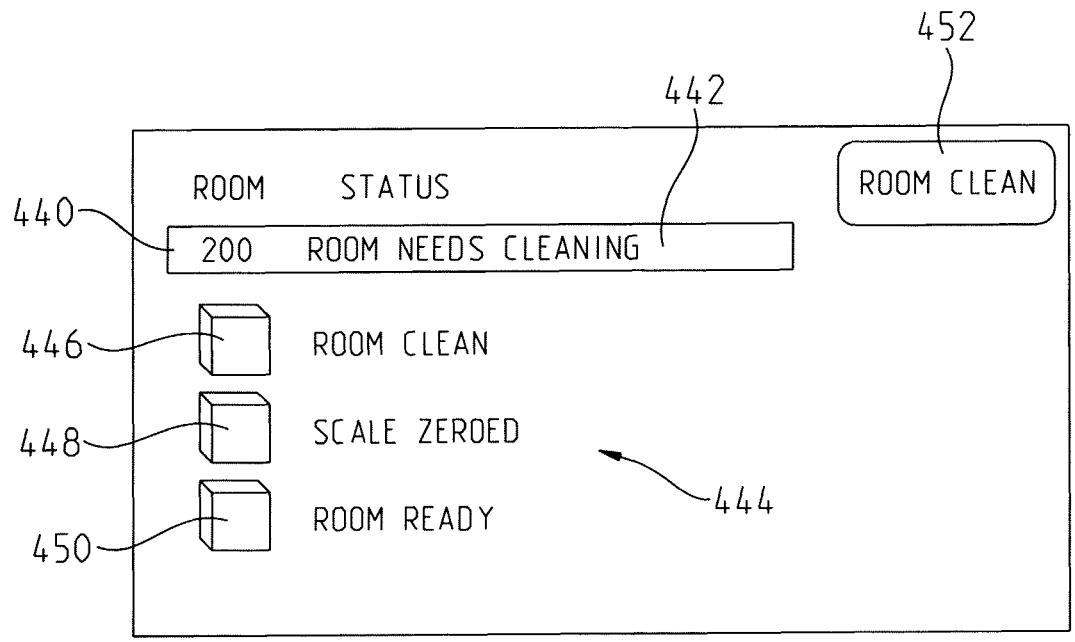
Figure 11B:
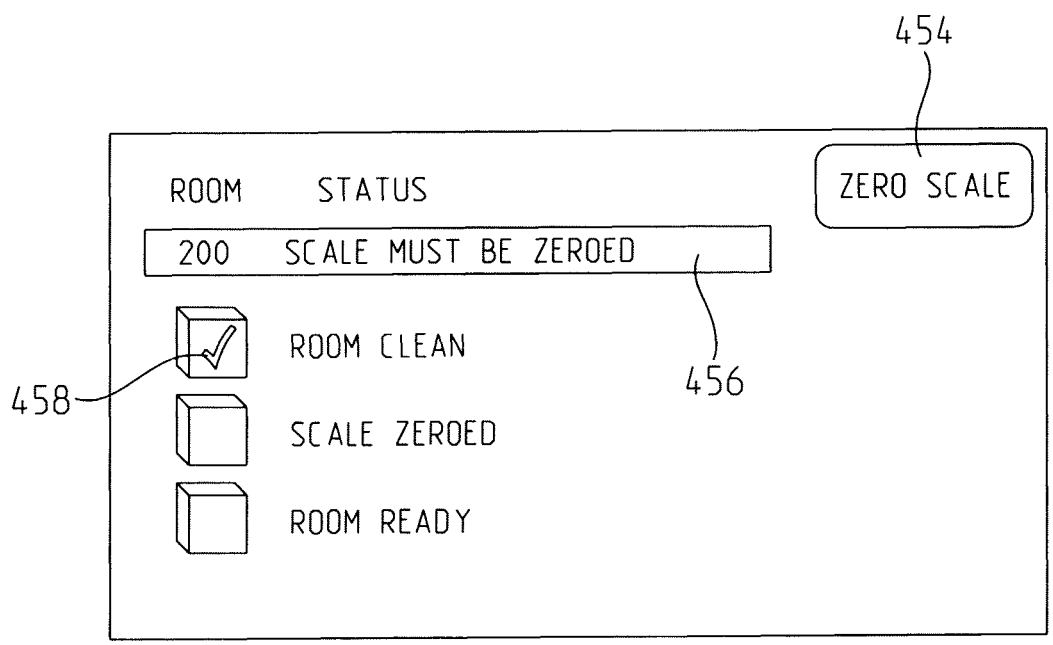

The configuration of the user control 452 changes as the room status changes. For example, in FIG. 11A, the room 200 is indicated as needing cleaning. As a result, the user control 452 displays "room clean," and activation of the room clean control by a user marks the room clean action item 446 as complete with a graphical checkmark (or other suitable indicator) 458 as shown in FIG. 11B. Once the room status has been updated to "clean," then the system 10 changes the room status from 442 (needs cleaning) to 456 (zero scale), and displays the zero scale user control 454 rather than the room clean user control 452.

Figure 11C:
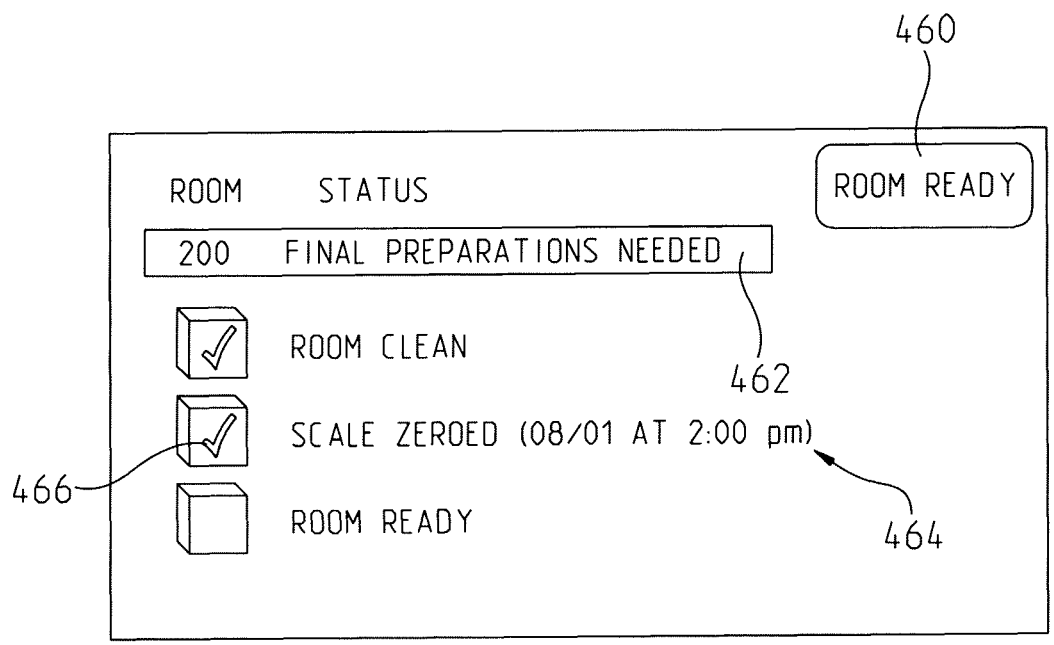

Activation of the zero scale control 454 by a user marks the zero scale action item 448 as complete with a graphical checkmark (or other suitable indicator) 466 and displays the date and time stamp of the scale zeroing 464 as shown in FIG. 11C. Once the room status has been updated to "room clean/ scale zeroed," or "scale zeroed," then the system 10 changes the room status from 456 (zero scale) to 462 (final preparations needed), and displays the room ready user control 460 rather than the zero scale user control 454.

Figure 11D:
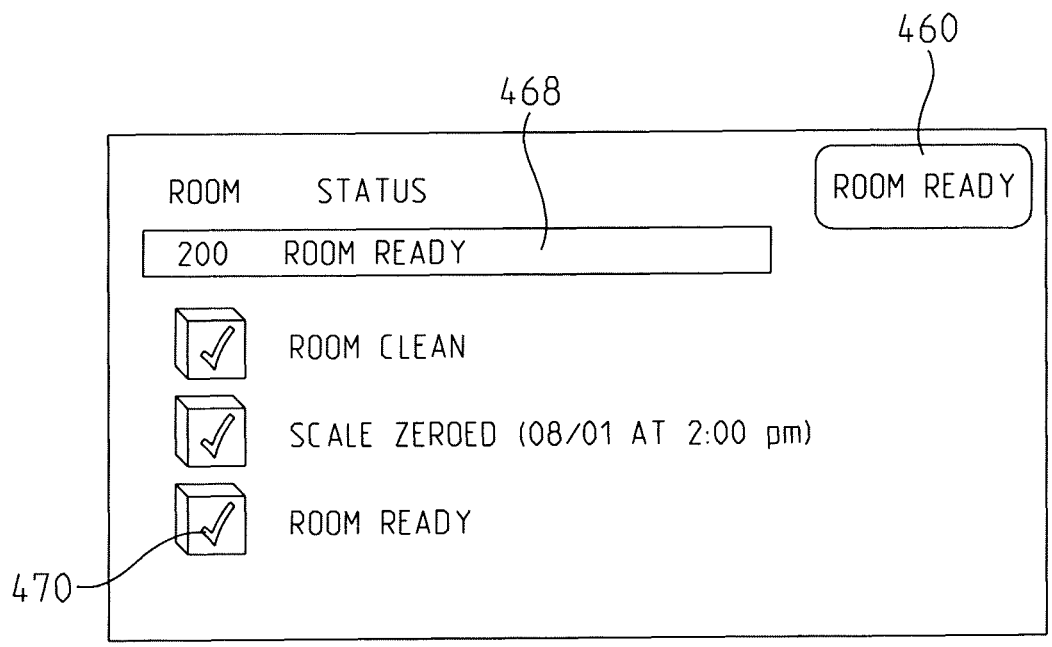

When the caregiver or other staff person has completed the final room preparations for a new patient, he or she activates the room ready control 460. Activation of the room ready control 460 updates the room status to 468 (room ready) and marks the room ready action item 450 as complete with a graphical indicator 470, as shown in FIG. 11D. When the room status is "ready" the room ready user control 460 may continue to be available for selection.

The system 10 may require a second activation of the room ready control 460 by a user to confirm that the room is ready for a new patient, before sending the room ready indication to the HIS system 50 and/or updating the server 18 and/or other interested systems or devices. Once the room ready control 460 is activated (e.g. one or two times as configured according to the requirements of a particular design), the display shown in FIG. 11E may be displayed.

Figure 11E:
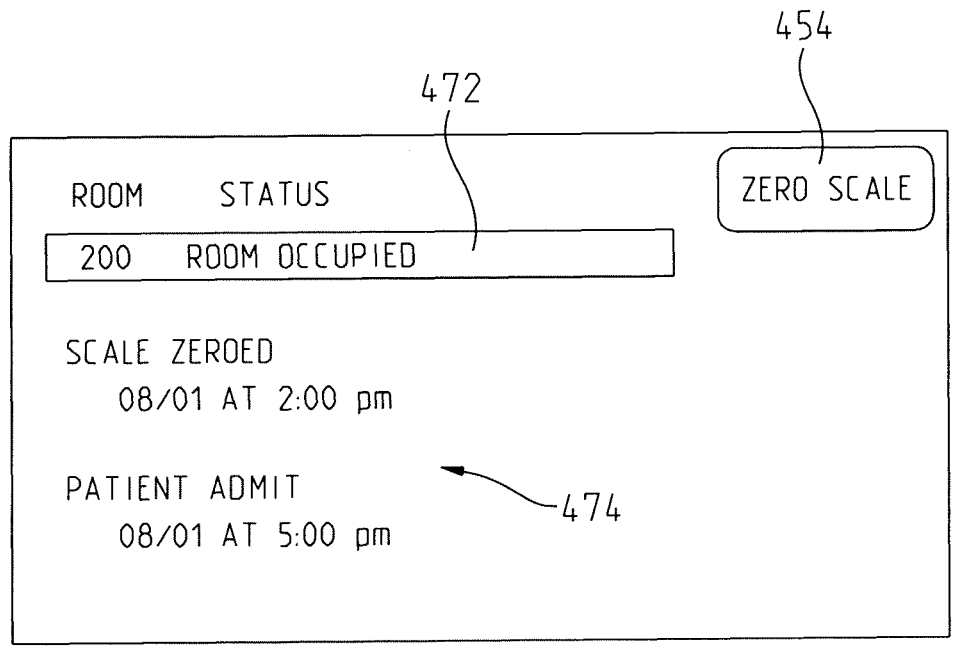

As indicated in FIG. 11E, the system 10 has detected that a patient has been admitted and assigned to the room. The room status 472 is updated to "occupied" and the data and time information for the last bed scale zeroing and the patient admit are displayed at a status area 474. The zero scale user control 454 is now displayed rather than the room ready control 460, because the system 10 is configured to cause admission of a patient into a room to change the room status from "ready" to "not ready" or "occupied."

Figure 11F:
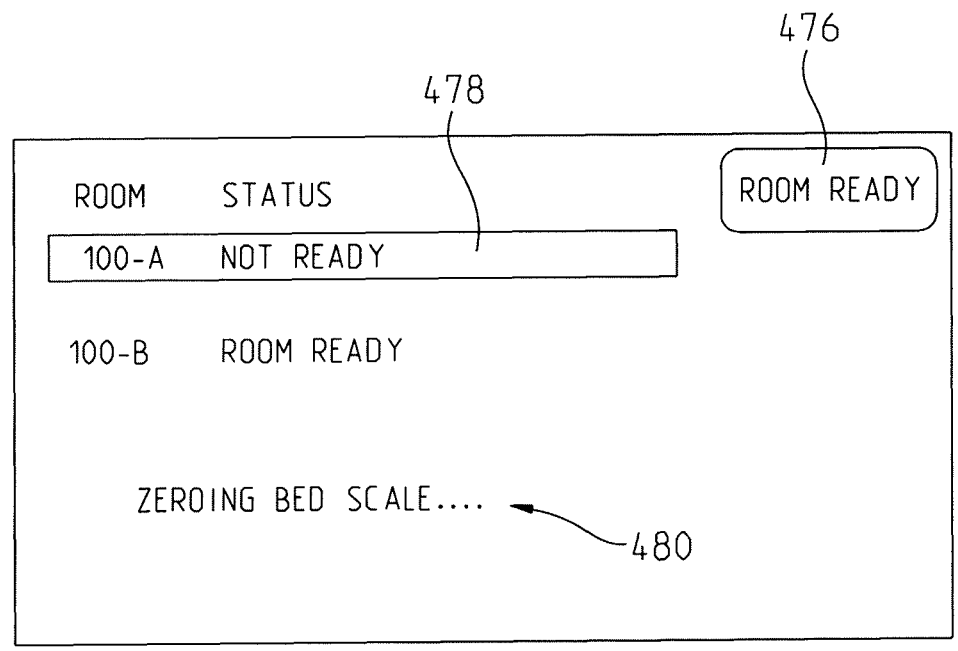

FIG. 11F illustrates another suitable display screen for the non-bed mounted user interface 166, which is room-based rather than bed-based in that it displays data for and enables control of multiple beds (or other equipment or devices located in the room). In this version of a room status display, each room (e.g. room and bed location in the room) is indicated as either not ready or ready using text rather than graphical indicators.

To select a particular bed from the list of beds in the room, the user touches the screen in the area of the desired room-bed number. When a bed is selected, the status line for the selected bed is highlighted or otherwise distinguished from other bed line items in the list (shown by area 478). In this version, selecting the room ready user control 476 automatically issues a request to the bed to zero the bed scale. A message indicating the progress of the requested bed function, e.g. that the zero command has been issued to the bed, is displayed at a status area 480. This progress indicator may be implemented graphically alternatively or in addition to a text message.

In some versions, a zero scale button replaces the room ready button after the room ready button is selected. Selection of the zero scale button may not cause the room's status to be automatically communicated (e.g. to an electronic status board, indicator assembly, mobile device or other input-output device). If the bed scale zeroing fails, the screen may still display the date and time stamp of the last time the bed scale was successfully zeroed.

Figure 12:
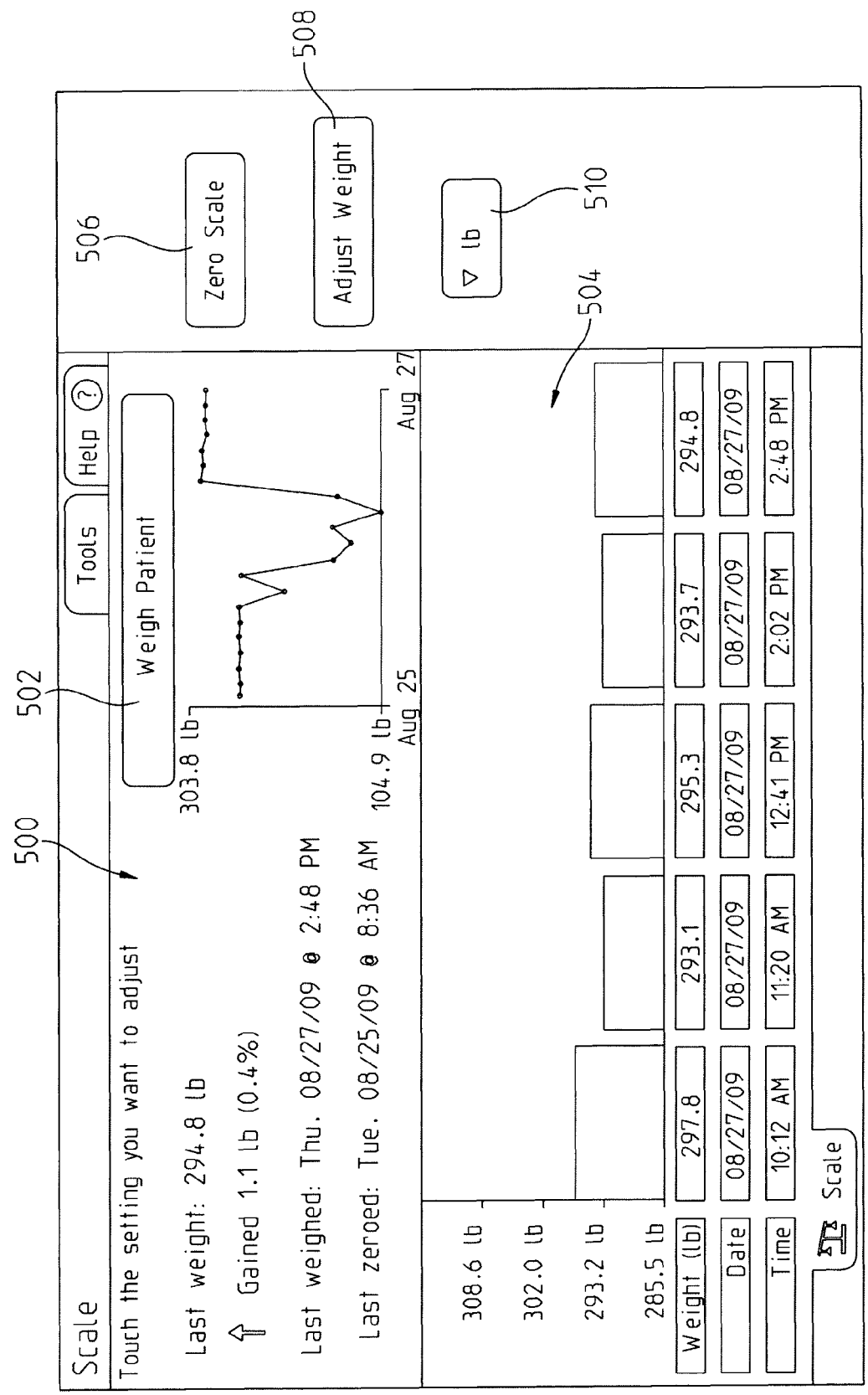

FIG. 12 illustrates a bed scale display screen that may be used on a non-bed mounted user interface 206 (e.g. 150, 152, 166). This display screen includes a combination of patient status information 500, patient history information 504, and user controls 506, 508, 510. Due to the amount of information and functionality provided on the single display screen of FIG. 12, this display screen is well-suited for a non-bed mounted user interface rather than a bed-mounted user interface. As shown, this display allows the caregiver to view the patient's current weight statistics and weight history, zero the bed scale and configure the weigh scale from a single screen rather than having to "tab" through multiple display screens as may be the case if a bed-mounted user interface were used.

Figure 13:
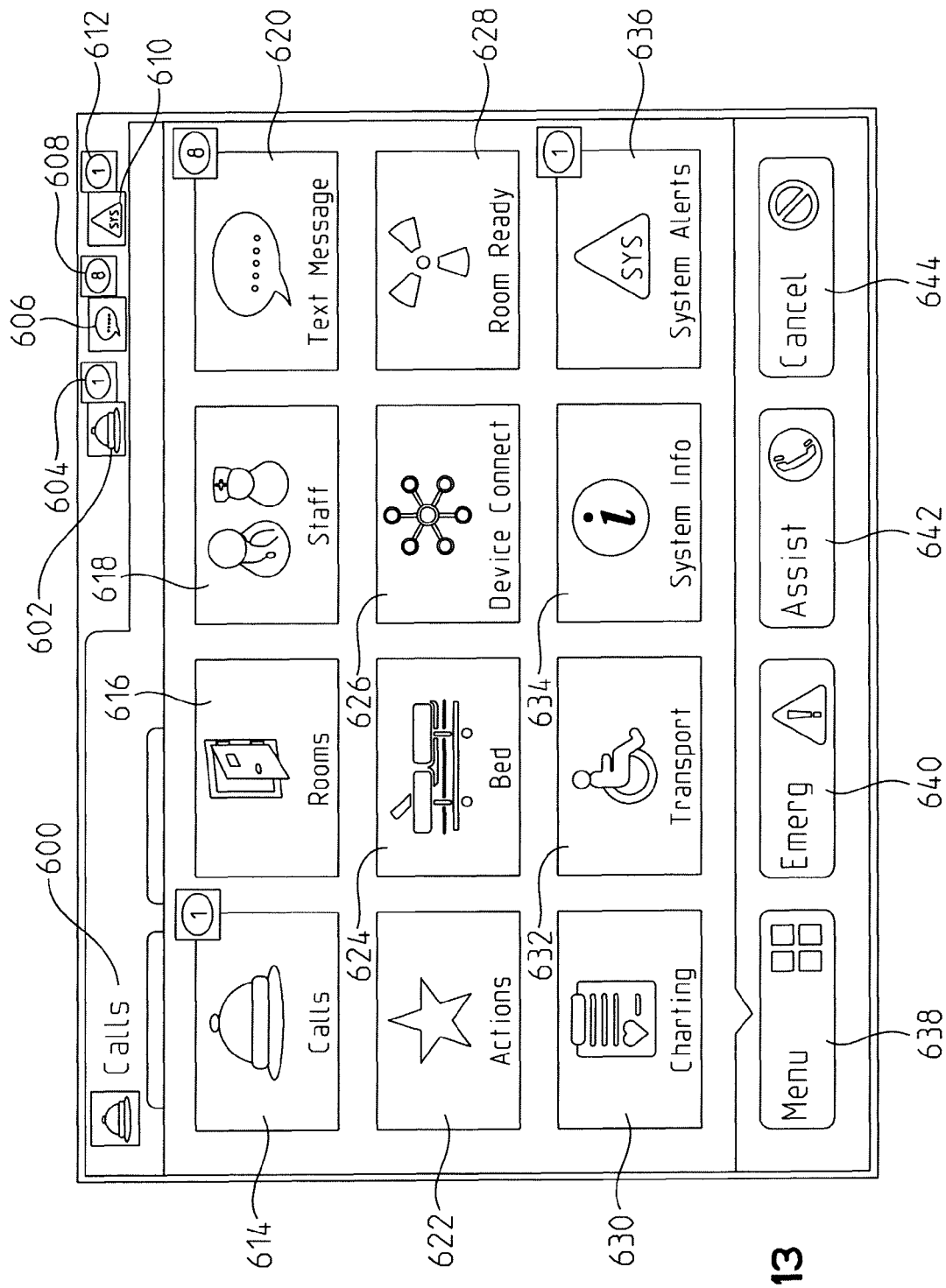
FIGS. 13-14 are sample screen displays for a healthcare information and communication system including patient room and bed management features.

FIGS. 13 and 14 illustrate screen displays that are suitable for use on a non-bed mounted user interface (e.g. 34, 36, 206) in connection with the system 10. In one version of the system 10, the screen display shown in FIG. 14 may be used on a master station 26, while the screen display shown in FIG. 13 may be used on a patient station 34, 36. However, in other versions, aspects of either or both of the screen displays shown in FIGS. 13 and 14 may be used on master stations, patient stations, staff stations, or other user interface devices used in connection with the system 10. Also, some or all of the aspects of the screen displays of FIGS. 13-14 may be used on the non-bed mounted user interfaces 150, 152, 166.

Referring to FIG. 13, the display screen shown thereon includes one or more selectable tabs or buttons 600, 638, 640, 642, 644, a status summary section including a number of miniature graphical icons 602, 604, 606, 608, 610 and 612, and a number of selectable cell-phone or PDA-style graphical icons 614, 616, 618, 620, 622, 624, 626, 628, 630, 632, 634, 636. The status summary section indicates the number of calls and/or alerts currently pending at the user interface (e.g. 26, 34, 36, 206) by type. The miniature icons 602, 604 indicate that one call is pending. The miniature icons 606, 608 indicate that eight text messages are pending. The miniature icons 610, 612 indicate that one system alert is pending.

Activation of the menu button 638 causes the icons to be displayed as shown. Activation of the emergency icon 640 automatically places an emergency call to a code blue operator and/or to the system 10. Activation of the assist button 642 places a call to the nurses' station responsible for monitoring the room in which the user interface is located. Activation of the cancel button 644 causes the system 10 to cancel the function last selected.

The calls icon 614 causes a calls screen such as the one shown in FIG. 14 to be displayed, e.g. to display a list of all pending calls, the call type and location. The rooms icon 616 displays a list of all of the rooms in the area of the healthcare facility being monitored and their current status. The staff icon 618 displays a list of caregivers and other staff members, as well as their current status and/or location.

The text message or "message center" icon 620 facilitates free-form and/or template-based text messaging among staff members connected to the system 10. In some versions of the system 10, the text messaging feature is used to view and process incoming messages, and/or to send text messages from a master station to one or more patient station(s), staff station(s), and/or remote input/output device(s) of the system 10. In other versions of the system 10, the text messaging feature may be available at patient stations or staff stations, to view, process, and/or send text messages to the master station, or to remote device(s) associated with caregiver(s) and/or staff person(s) in the facility, alternatively or in addition to sending text messages from a master station to such devices.

The messages may be viewed, retrieved, and/or handled (e.g. responded to, canceled, deleted, forwarded, saved) by authorized caregivers or staff persons in accordance with the business rules that are used to configure the system 10 for the facility. In some versions of the system 10, the icon 620 is configured to provide access to any type of electronic notification received by the system 10, including but not limited to text messages, system alerts, bed status alerts, safety alerts, and any notifications received from remote systems, such as notifications that a patient's test or lab results are available, among others.

The text messaging feature accessible via the icon 620 uses a wireless interface directly to pagers or other mobile communication devices, and is highly configurable in that the messages that can be sent may be unrelated to any particular patient. For example, a user of the system 10 may generate a text message that contains a link to an indicator assembly, to illuminate the indicator assembly in connection with the text message. Also, the text messages may be longer in length than those permitted by messaging features of prior systems.

The actions icon 622 provides access to one or a number of additional icons, each of which initiates a different feature of the system 10. For example, one icon 622 provides access to the room ready features and/or other aspects of the system 10, including but not limited to features that are specifically customized for a particular facility. Icons that are customized for a particular facility may include thereon a specific "custom" graphic representing the custom feature, as may be required or desirable for a given facility.

In one version, once the actions icon 622 is selected, the user can initiate one or a number of electronic requests or messages, such as a request to housekeeping to clean a room, enter input to indicate that certain tasks or action items have been completed (e.g. nurses' rounding, etc), issue a dietary request, issue a transport request, change the status of a room (e.g. from clean to needs cleaning), and/or review notifications received from other systems, such as notifications that doctor's orders have been completed (e.g. diagnostic procedures such as x-rays and ultrasounds, lab work, or consultations). These requests are mapped to icons and call types by the system 10. The system 10 routes the requests to the appropriate recipients, which may include external systems such as one or more of those described above. The system 10 also facilitates handling of the requests at one or more of the various user interfaces of the system 10 described above, by displaying the status of the messages and/or requests (e.g., sent or received).

The bed icon 624 provides access to bed functions such as activate or deactivate bed exit alarm or head of bed angle alarm, zero the bed scale, clear patient history data, and/or configure alerts and/or alarms. The device connect icon 626 allows the user to view the status of beds and other devices that are connected to the system 10 and to activate interfaces to external systems. For example, patient weight information or other information captured at the bed may be sent from the bed to an EMR system through an interface with the healthcare facility's EMR vendor.

The room ready icon 628 provides access to all of the room ready features described in this disclosure. The charting icon 630 provides an interface between equipment or devices connected to the system 10 and the healthcare facility's EMR system for the purpose of sending patient chart information (e.g. vital signs) directly from the monitoring device to the EMR via the system 10.

The transport icon 632 enables a caregiver or other staff members to issue transport requests when a patient in the room needs to be transported from the room to some other location in the facility, obtain updates on the status of transport requests, and obtain information about equipment included in transports (such as wheelchairs, IV poles, etc.). The system information icon 638 displays system information such as configuration settings, current version information, user help screens, and maintenance information. The system alerts icon 636 displays system alerts that are pending. System alerts may include, for example, an indication that a new version of system software is available or being uploaded, an indication that a particular bed or device has been connected or disconnected from the system 10, or that a system-based error has occurred.

The display screen shown in FIG. 14 has a call list 704, and a summary status area 702 similar to that shown in FIG. 13. The display screen of FIG. 14 also includes a number of selectable cell-phone or PDA-style icons 7143, 716, 718, 720, 722, 724, 726, 728, 730, 732, and a number of selectable buttons 706, 708, 710, 712, 734, 736, 738, 740, 742.

Many of the icons and buttons shown in FIG. 14 relate to nurse call features of the system 10. The acknowledge button 706 allows a user to acknowledge an incoming call. The hide details button 708 allows a user to manage the call list display by hiding certain details. The silence tones button 710 allows a user to mute any audible tones that may be issued by the system 10 at the user interface. The speaker phone button 712 allows the user to use a speaker phone while answering an incoming call. The menu button 734 causes the menu of available icons to be displayed. The calls button 736 operates similarly to the calls button 614 described above. The answer button 738 allows a user to answer a pending call. The hold button 740 allows the user to put an incoming call on hold. The volume button 742 allows the user to change the volume of an answered call.

The rooms, staff, system info, and system alerts icons 714, 716, 730, and 732 operate similarly to the icons having the same names described above. The paging icon 718 enables the sending of overhead paging communications using the healthcare facility's overhead paging system, and/or enables the sending of pages through the communication network of the system 10 to patient and/or staff stations, and/or enables the sending of pages from the system 10 to other devices that are directly or indirectly connected to the system 10. The reminder list icon 720 allows a caregiver or other staff person to access and maintain a reminder list. The attended/away icon 722 allows a caregiver or other staff person to indicate when they are on duty and when they are not on duty. The swing rooms icon 724 and capture units icon 726 allow a master station 26 to assume monitoring for rooms of another nursing unit or an entire nursing unit, in the event that a master station is not available for the other nursing unit, or for other reasons. The reset rooms icon 728 allows a user to reset selected devices (such as patient stations, non-bed mounted user interfaces, patient devices and other devices) located in the room, automatically from a user interface of the system 10.

There are many advantages of the present disclosure arising from the various features described herein. It will be noted that alternative embodiments of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A bed system comprising
a bed having a plurality of electronically-controllable functions and a bed identifier, and
a bed control system connected to the bed and configured to control one or more of the electronically-controllable functions of the bed, the bed controller comprising
memory in which data and computer-executable instructions are stored,
a communications interface configured to couple the bed system to a health information system of a healthcare facility, and
processor circuitry configured to execute the computer-executable instructions to receive via the communications interface a patient status signal representative of patient status information from the health information system, the patient status information indicating a status of a patient in the healthcare facility, and send a control signal to the bed to cause the bed to automatically without user intervention initiate one of the electronically-controlled functions performed by the bed in response to the patient status signal; wherein the patient status signal includes an admission, discharge and transfer (ADT) indicator, the bed has a built-in weigh scale, and the bed zeros the weigh scale in response to the patient status signal.

2. The bed system of claim 1, wherein the patient status signal indicates that the patient has been discharged from the healthcare facility.

3. A healthcare communication system comprising
memory in which data and computer-executable instructions are stored,
a communications interface, and
processor circuitry configured to execute the computer-executable instructions to:
receive via the communications interface a patient status signal representative of patient status information generated at a health information system of a healthcare facility, the patient status signal indicating a status of a patient in the healthcare facility,
determine, based on the patient status signal, a status of a room in the healthcare facility, the room having therein a bed associated with the patient,
send via the communications interface a room status signal indicating the status of the room to a user interface device located in the patient room to cause the user interface device to indicate the status of the room, generate a list of actions to be performed by a person associated with the healthcare facility in the room associated with the patient, the list of actions being generated in accordance with the room status, the person being someone other than the patient, the list of actions including at least one bed-related activity to be performed by the bed and at least one room-related activity to be performed by the person, and send via the communications interface the list of actions to an input/output device.

4. The healthcare communication system of claim 3, wherein the status of the patient is one of admitted, transferred, or discharged.

5. The healthcare communication system of claim 4, wherein the status of the room is one of clean, needs cleaning, and ready for new patient.

6. The healthcare communication system of claim 3, wherein the list of actions includes at least one patient-related activity.

7. The healthcare communication system of claim 6, wherein the at least one patient-related activity includes at least one of taking patient's temperature, giving patient a pillow, and giving patient a garment.

8. The healthcare communication system of claim 3, wherein the processor circuitry is configured to execute computer-executable instructions to receive user input at the user interface device, and the user input relates to at least one of a room status, a patient status and a bed status.

9. The healthcare communication system of claim 8, wherein the processor circuitry is configured to execute computer-executable instructions to send via the communications interface a signal indicative of the user input to the health information system of the healthcare facility.

10. The healthcare communication system of claim 3, wherein the at least one bed-related activity relates to at least one of raising the bed siderails, setting a bed brake, placing the bed in a low position, arming or disarming a bed patient position monitoring (PPM) system, arming or disarming a head of bed angle monitoring system, placing sheets on the bed, and zeroing a weigh scale of the bed.

11. The healthcare communication system of claim 3, wherein the at least one room-related activity relates to at least one of clean the room, remove obstructions to room exit, prepare bed for new patient, indicate whether room preparations are complete, and indicate whether a caregiver's round is complete.

12. The healthcare communication system of claim 3, wherein the processor circuitry is configured to execute computer-executable instructions to send via the communications interface a signal to the bed to cause the bed to execute an electronically-controlled bed function.

13. The healthcare communication system of claim 3, wherein the processor circuitry is configured to execute computer-executable instructions to send via the communications interface an indication of the room status to a mobile device of a person associated with the facility.

14. The healthcare communication system of claim 3, wherein the processor circuitry is configured to execute computer-executable instructions to send via the communications interface an indication of the room status to an output device located outside the patient's room.

* * * * *